US012595307B2

(12) United States Patent
Olson et al.

(10) Patent No.: US 12,595,307 B2
(45) Date of Patent: Apr. 7, 2026

(54) ANTI-CTLA4 MONOCLONAL ANTIBODIES AND CHIMERIC ANTIGEN RECEPTORS

(71) Applicant: NantBio, Inc., Culver City, CA (US)

(72) Inventors: Clifford Anders Olson, Culver City, CA (US); Shiho Tanaka, Culver City, CA (US); Kayvan Niazi, Culver City, CA (US); Melanie Hermreck, Culver City, CA (US); Thomas H. King, Culver City, CA (US); Zhimin Guo, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 642 days.

(21) Appl. No.: 18/001,566

(22) PCT Filed: Jun. 9, 2021

(86) PCT No.: PCT/IB2021/055076
§ 371 (c)(1),
(2) Date: Dec. 12, 2022

(87) PCT Pub. No.: WO2021/250594
PCT Pub. Date: Dec. 16, 2021

(65) Prior Publication Data
US 2024/0084011 A1      Mar. 14, 2024

Related U.S. Application Data

(60) Provisional application No. 63/038,111, filed on Jun. 11, 2020.

(51) Int. Cl.
| | |
|---|---|
| *C07K 16/28* | (2006.01) |
| *A61K 49/00* | (2006.01) |
| *A61P 35/00* | (2006.01) |

(52) U.S. Cl.
CPC ...... *C07K 16/2818* (2013.01); *A61K 49/0002* (2013.01); *A61P 35/00* (2018.01); *C07K 2317/35* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 8,697,845 B2 | 4/2014 | Ward et al. | |
| 2011/0044953 A1 | 2/2011 | Allison et al. | |
| 2017/0226211 A1 | 8/2017 | Wang et al. | |

FOREIGN PATENT DOCUMENTS

| | | |
|---|---|---|
| JP | 2009532030 A | 9/2010 |
| JP | 2017523807 A | 8/2017 |
| JP | 2020508637 A | 3/2020 |
| JP | 2020508655 A | 3/2020 |
| JP | 2020513819 A | 5/2020 |

(Continued)

OTHER PUBLICATIONS

Examination report No. 1 received for Australia patent application No. 2021287376 dated Oct. 29, 2024, 04 Pages.

(Continued)

*Primary Examiner* — Karl J Puttlitz
(74) *Attorney, Agent, or Firm* — Umberg Zipser LLP; Martin Fessenmaier; Priti Phukan

(57) ABSTRACT

Compositions and methods are presented in which selected polypeptide compounds bind to CTLA-4. Most typically, binding is mediated by selected VH and/or VL domains, and preferred compounds are prepared as scFv, IgG, or CAR.

8 Claims, 7 Drawing Sheets

Specification includes a Sequence Listing.

Human CD80

Mouse CD80

Baseline normalized

| | Step 1 capture: | Step 2 block (mAb VL/VH): | Step 3 bind: |
|---|---|---|---|
| | CTLA-4 | buffer | CD80 |
| | CTLA-4 | 78-8/78-8D2 | CD80 |
| | CTLA-4 | 78-8/78-8D4 | CD80 |
| | CTLA-4 | 78-8/78-8D22 | CD80 |
| | CTLA-4 | 78-24/78-24D1V | CD80 |
| | CTLA-4 | 78-24/78-24D17V | CD80 |
| | CTLA-4 | 78-24/78-24D22V | CD80 |
| | buffer | buffer | buffer |

(56)                References Cited

FOREIGN PATENT DOCUMENTS

| WO | 2012/120125 A1 | 9/2012 |
| WO | 2016015675 A1 | 2/2016 |
| WO | 2016/145030 A1 | 9/2016 |
| WO | 2017/084078 A1 | 5/2017 |
| WO | 2018068182 A1 | 4/2018 |
| WO | 2018156250 A1 | 8/2018 |
| WO | 2018165895 A1 | 9/2018 |
| WO | 2020112987 A1 | 6/2020 |

OTHER PUBLICATIONS

NCBI, "immunoglobulin heavy chain [*Homo sapiens*]", GenBank Accession No. QBK47405.1, Jan. 23, 2017, pp. 1-4.
Linch et al., "Combination OX40 agonism/CTLA-4 blockade with HER2 vaccination reverses T-cell anergy and promotes survival in tumor-bearing mice", PNAS, 113 (3) E319-E327.
Melero et al., "Agonist Antibodies to TNFR Molecules That Costimulate T and NK Cells", 2013, Clin Cancer Res; 19(5) 1044-1053.
NCBI, "immunoglobulin kappa 1 light chain, partial [*Homo sapiens*]", GenBank Accession No. ABU90625.1, Jan. 23, 2017, pp. 1-3.
Extended European Search Report received for EP Application No. 21823105.8 dated Jul. 3, 2024, 10 Pages.
Chen et al., "Expression, purification, and in vitro refolding of a humanized single-chain Fv antibody against human CTLA4 (CD152)", Protein Expression and Purification 46 (2006) 495-502.
Griffin et al., "Blockade of T Cell Activation Using a Surface-Linked Single-Chain Antibody to CTLA-4 (CD152)", The Journal of Immunology, 2000, 164: 4433-4442.

Notice of Reason of Refusal received for JP Application No. 2022-576221 dated Jun. 25, 2024, 17 Pages (including english translation).
International Search Report & Written Opinion received for PCT/IB2021/055076 dated Sep. 7, 2021, 13 pages.
International Preliminary Report on Patentability received for PCT/IB2021/055076 dated Sep. 26, 2022, 4 pages.
Examination Report received for GB Application Serial No. 2218296.8 dated Nov. 1, 2024, 05 pages.
Examination Report received for CA Application No. 3,186,777 dated Jun. 13, 2024, 04 pages.
Examination Report received for GB Application Serial No. 2218296.8 dated Aug. 15, 2024, 06 pages.
Decision to Grant received in Japanese Patent Application No. 2022-576221 dated May 20, 2025, 6 pages including English translation.
Examination report No. 2 received for Australia patent application No. 2021287376 dated Dec. 2, 2024, 03 Pages.
Examination report No. 3 received for Australia patent application No. 2021287376 dated Feb. 13, 2025, 13 Pages.
Decision of Refusal received for JP Application No. 2022-576221 dated Nov. 29, 2024, 11 Pages (including english translation).
Examination Report for Canadian Application No. 3186777 dated Jun. 25, 2025, 6 pages.
Li, D., Li, J., Chu, H., & Wang, Z. (2020). A functional antibody cross-reactive to both human and murine cytotoxic T-lymphocyte-associated protein 4 via binding to an N-glycosylation epitope. mAbs, 12(1).
Fourth Examination Report received for Australian Application Serial No. 2021287376 dated Mar. 21, 2025, 3 pages.

Baseline normalized

| | Step 1 capture: | Step 2 block (mAb VL/VH): | Step 3 bind: |
|---|---|---|---|
| ▬▬ | CTLA-4 | buffer | CD80 |
| ▬▬ | CTLA-4 | 78-8/78-8D2 | CD80 |
| ▬▬ | CTLA-4 | 78-8/78-8D4 | CD80 |
| ▬▬ | CTLA-4 | 78-8/78-8D22 | CD80 |
| ▬▬ | CTLA-4 | 78-24/78-24D1V | CD80 |
| ▬▬ | CTLA-4 | 78-24/78-24D17V | CD80 |
| ▬▬ | CTLA-4 | 78-24/78-24D22V | CD80 |
| ▬▬ | buffer | buffer | buffer |

SEQUENCE LISTING

<160> NUMBER OF SEQ ID NOS: 71

<210> SEQ ID NO 1
<211> LENGTH: 125
<212> TYPE: PRT
<213> ORGANISM: Artificial Sequence
<220> FEATURE:
<223> OTHER INFORMATION: 73-2 VH amino acid sequence - Artificial
      sequence translated from an isolated clone of an RNA display
      library -continued

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met His Trp Val Arg Gln Ala Pro Gly Lys Gly Leu Glu Trp Val
        35                  40                  45

Ser Tyr Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Met Leu Val Asp Ser Val Asn Arg Val Phe Gly Phe
            100                 105                 110

Asp Val Trp Gly Gln Gly Thr Leu Val Thr Val Ser Ser
        115                 120                 125
```

```
<210> SEQ ID NO 2
<211> LENGTH: 107
<212> TYPE: PRT
<213> ORGANISM: Artificial Sequence
<220> FEATURE:
<223> OTHER INFORMATION: 73-2 VL amino acid sequence - Artificial
      sequence translated from an isolated clone of an RNA display
      library
```

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Thr Asn Phe Pro Phe
                85                  90                  95

Thr Phe Gly Gln Gly Thr Lys Val Glu Ile Lys
            100                 105
```

```
<210> SEQ ID NO 3
<211> LENGTH: 125
<212> TYPE: PRT
<213> ORGANISM: Artificial Sequence
<220> FEATURE:
<223> OTHER INFORMATION: 74-1 VH amino acid sequence - Artificial
      sequence translated from an isolated clone of an RNA display
      library
```

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Tyr Met His Trp Val Arg Gln Ala Pro Gly Lys Gly Leu Glu Trp Val
```

```
                35                    40                    45

Ser Tyr Ile Ser Gly Ser Gly Ser Ser Thr Tyr Tyr Ala Asp Ser Val
    50                    55                    60

Lys Gly Arg Phe Thr Ile Ser Arg Asp Asn Ser Lys Asn Thr Leu Tyr
65                    70                    75                    80

Leu Gln Met Asn Ser Leu Arg Ala Glu Asp Thr Ala Val Tyr Tyr Cys
                85                    90                    95

Ala Arg Asp Arg Met Leu Val Asp Ser Val Asn Arg Val Phe Gly Phe
            100                   105                   110

Asp Val Trp Gly Gln Gly Thr Leu Val Thr Val Ser Ser
            115                   120                   125

<210> SEQ ID NO 4
<211> LENGTH: 107
<212> TYPE: PRT
<213> ORGANISM: Artificial Sequence
<220> FEATURE:
<223> OTHER INFORMATION: 74-1 VL amino acid sequence - Artificial
      sequence translated from an isolated clone of an RNA display
      library

<400> SEQUENCE: 4

Asp Ile Gln Met Thr Gln Ser Pro Ser Ser Leu Ser Ala Ser Val Gly
1                   5                     10                    15

Asp Arg Val Thr Ile Thr Cys Gln Ala Ser Gln Asp Ile Ser Asn Tyr
                20                    25                    30

Leu Asn Trp Tyr Gln Gln Lys Pro Gly Lys Ala Pro Lys Leu Leu Ile
            35                    40                    45

Tyr Asp Ala Ser Asn Leu Glu Thr Gly Val Pro Ser Arg Phe Ser Gly
    50                    55                    60

Ser Gly Ser Gly Thr Asp Phe Thr Phe Thr Ile Ser Ser Leu Gln Pro
65                    70                    75                    80

Glu Asp Ile Ala Thr Tyr Tyr Cys Gln Gln His Thr Asn Phe Pro Phe
                85                    90                    95

Thr Phe Gly Gln Gly Thr Lys Val Glu Ile Lys
            100                   105

<210> SEQ ID NO 5
<211> LENGTH: 124
<212> TYPE: PRT
<213> ORGANISM: Artificial Sequence
<220> FEATURE:
<223> OTHER INFORMATION: 78-1 VH amino acid sequence - Artificial
      sequence translated from an isolated clone of an RNA display
      library

<400> SEQUENCE: 5

Glu Val Gln Leu Val Glu Ser Gly Gly Gly Leu Val Gln Pro Gly Gly
1                   5                     10                    15

Ser Leu Arg Leu Ser Cys Ala Ala Ser Gly Phe Thr Phe Ser Ser Tyr
                20                    25                    30

Tyr Met His Trp Val Arg Gln Ala Pro Gly Lys Gly Leu Glu Trp Val
            35                    40                    45

Ser Ala Ile Ser Thr Ser Gly Arg Ser Thr Tyr Tyr Ala Asp Ser Val
    50                    55                    60

Lys Gly Arg Phe Thr Ile Ser Arg Asp Asn Ser Lys Asn Thr Leu Tyr
65                    70                    75                    80

Leu Gln Met Asn Ser Leu Arg Ala Glu Asp Thr Ala Val Tyr Tyr Cys
                85                    90                    95
```

-continued

```
Ala Arg Gly Arg Arg Ala Gly Met Val Ala Phe Trp Asp Gly Phe Asp
            100                 105                 110

Val Trp Gly Gln Gly Thr Leu Val Thr Val Ser Ser
        115                 120

<210> SEQ ID NO 6
<211> LENGTH: 107
<212> TYPE: PRT
<213> ORGANISM: Artificial Sequence
<220> FEATURE:
<223> OTHER INFORMATION: 78-1 VL amino acid sequence - Artificial
      sequence translated from an isolated clone of an RNA display
      library

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Thr Leu Pro Phe
                85                  90                  95

Thr Phe Gly Gln Gly Thr Lys Val Glu Ile Lys
            100                 105

<210> SEQ ID NO 7
<211> LENGTH: 125
<212> TYPE: PRT
<213> ORGANISM: Artificial Sequence
<220> FEATURE:
<223> OTHER INFORMATION: 78-2 VH amino acid sequence - Artificial
      sequence translated from an isolated clone of an RNA display
      library

<400> SEQUENCE: 7

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ala Ser
            20                  25                  30

Tyr Ala Met His Trp Val Arg Gln Ala Pro Gly Lys Gly Leu Glu Trp
        35                  40                  45

Val Ser Ile Ile Ser Gly Ser Gly Gly Ser Thr Asp Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Arg His Ile Pro Val Ser Arg Phe Asn Ala Ala Phe
            100                 105                 110

Asp Val Trp Gly Gln Gly Thr Leu Val Thr Val Ser Ser
        115                 120                 125

<210> SEQ ID NO 8
<211> LENGTH: 107
```

<212> TYPE: PRT
<213> ORGANISM: Artificial Sequence
<220> FEATURE:
<223> OTHER INFORMATION: 78-2 VL amino acid sequence - Artificial
      sequence translated from an isolated clone of an RNA display
      library

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ala Ser Trp Pro Trp
                85                  90                  95

Thr Phe Gly Gln Gly Thr Lys Val Glu Ile Lys
            100                 105

<210> SEQ ID NO 9
<211> LENGTH: 123
<212> TYPE: PRT
<213> ORGANISM: Artificial Sequence
<220> FEATURE:
<223> OTHER INFORMATION: 78-5 VH amino acid sequence - Artificial
      sequence translated from an isolated clone of an RNA display
      library

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Trp Gly Ser Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Glu Ser Phe Arg Thr Asn Lys Gly Phe Asp Val
            100                 105                 110

Trp Gly Gln Gly Thr Leu Val Thr Val Ser Ser
        115                 120

<210> SEQ ID NO 10
<211> LENGTH: 107
<212> TYPE: PRT
<213> ORGANISM: Artificial Sequence
<220> FEATURE:
<223> OTHER INFORMATION: 78-5 VL amino acid sequence - Artificial
      sequence

<400> SEQUENCE: 10

Asp Ile Gln Met Thr Gln Ser Pro Ser Ser Leu Ser Ala Ser Val Gly
1               5                   10                  15

```
Asp Arg Val Thr Ile Thr Cys Gln Ala Ser Gln Asp Ile Ser Asn Tyr
        20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asn Asn His Pro Phe
                85                  90                  95

Thr Phe Gly Gln Gly Thr Lys Val Glu Ile Lys
            100                 105

<210> SEQ ID NO 11
<211> LENGTH: 124
<212> TYPE: PRT
<213> ORGANISM: Artificial Sequence
<220> FEATURE:
<223> OTHER INFORMATION: 78-8 VH amino acid sequence - Artificial
      sequence translated from an isolated clone of an RNA display
      library

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
        20                  25                  30

Val Met His Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Leu Ile Gly Leu Ala Leu Tyr Gly Glu Ala Phe Asp
            100                 105                 110

Val Trp Gly Gln Gly Thr Leu Val Thr Val Ser Ser
        115                 120

<210> SEQ ID NO 12
<211> LENGTH: 107
<212> TYPE: PRT
<213> ORGANISM: Artificial Sequence
<220> FEATURE:
<223> OTHER INFORMATION: 78-8 VL amino acid sequence - Artificial
      sequence translated from an isolated clone of an RNA display
      library

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Gln Ala Ser Lys Asp Ile Ser Asn Tyr
        20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60
```

-continued

```
Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asn Ser Phe Pro Leu
                85                  90                  95

Thr Phe Gly Gln Gly Thr Lys Val Glu Ile Lys
            100                 105

<210> SEQ ID NO 13
<211> LENGTH: 124
<212> TYPE: PRT
<213> ORGANISM: Artificial Sequence
<220> FEATURE:
<223> OTHER INFORMATION: 78-8D2 VH amino acid sequence - Artificial
      sequence translated from an isolated clone of an RNA display
      library

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Val Met His Trp Val Arg Gln Ala Pro Gly Lys Gly Leu Glu Trp Val
            35                  40                  45

Ser Ala Ile Thr Trp Ser Gly Arg Gly Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Leu Phe Gly Leu Ala Leu Tyr Gly Glu Ala Phe Asp
                100                 105                 110

Val Trp Gly Gln Gly Thr Leu Val Thr Val Ser Ser
            115                 120

<210> SEQ ID NO 14
<211> LENGTH: 107
<212> TYPE: PRT
<213> ORGANISM: Artificial Sequence
<220> FEATURE:
<223> OTHER INFORMATION: 78-8D2 VL amino acid sequence - Artificial
      sequence translated from an isolated clone of an RNA display
      library

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Gln Ala Ser Lys Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Ile Ile Ser Ser Leu Gln Pro
65                  70                  75                  80

Glu Asp Ile Ala Thr Tyr Tyr Cys Gln Gln Phe Asn Ser Phe Pro Leu
                85                  90                  95

Thr Phe Gly Gln Gly Thr Lys Val Glu Ile Lys
            100                 105
```

```
<210> SEQ ID NO 15
<211> LENGTH: 124
<212> TYPE: PRT
<213> ORGANISM: Artificial Sequence
<220> FEATURE:
<223> OTHER INFORMATION: 78-8D4 VH amino acid sequence - Artificial
      sequence translated from an isolated clone of an RNA display
      library

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met His Trp Val Arg Gln Ala Pro Gly Lys Gly Leu Glu Trp Val
        35                  40                  45

Ser Ala Ile Thr Trp Ser Gly Gly Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Leu Phe Gly Leu Val Arg Tyr Gly Glu Ala Phe Asp
                100                 105                 110

Val Trp Gly Gln Gly Thr Leu Val Thr Val Ser Ser
        115                 120

<210> SEQ ID NO 16
<211> LENGTH: 107
<212> TYPE: PRT
<213> ORGANISM: Artificial Sequence
<220> FEATURE:
<223> OTHER INFORMATION: 78-8D4 VL amino acid sequence - Artificial
      sequence translated from an isolated clone of an RNA display
      library

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Gln Ala Ser Lys Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asn Ser Phe Pro Leu
                85                  90                  95

Thr Phe Gly Gln Gly Thr Lys Val Glu Ile Lys
                100                 105

<210> SEQ ID NO 17
<211> LENGTH: 124
<212> TYPE: PRT
<213> ORGANISM: Artificial Sequence
<220> FEATURE:
<223> OTHER INFORMATION: 78-8D5 VH amino acid sequence - Artificial
      sequence translated from an isolated clone of an RNA display
      library

<400> SEQUENCE: 17
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met His Trp Val Arg Gln Ala Pro Gly Lys Gly Leu Glu Trp Val
        35                  40                  45

Ser Ala Ile Ser Trp Ser Gly Gly Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Leu Phe Gly Leu Ala Leu Tyr Gly Glu Ala Phe Asp
            100                 105                 110

Val Trp Gly Gln Gly Thr Leu Val Thr Val Ser Ser
        115                 120
```

```
<210> SEQ ID NO 18
<211> LENGTH: 107
<212> TYPE: PRT
<213> ORGANISM: Artificial Sequence
<220> FEATURE:
<223> OTHER INFORMATION: 78-8D5 VL amino acid sequence - Artificial
      sequence translated from an isolated clone of an RNA display
      library

<400> SEQUENCE: 18
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Lys Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asn Ser Phe Pro Leu
                85                  90                  95

Thr Phe Gly Gln Gly Thr Lys Val Glu Ile Lys
            100                 105
```

```
<210> SEQ ID NO 19
<211> LENGTH: 124
<212> TYPE: PRT
<213> ORGANISM: Artificial Sequence
<220> FEATURE:
<223> OTHER INFORMATION: 78-8D6 VH amino acid sequence - Artificial
      sequence translated from an isolated clone of an RNA display
      library

<400> SEQUENCE: 19
```

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Val Met His Trp Val Arg Gln Ala Pro Gly Lys Gly Leu Glu Trp Val
        35                  40                  45
```

-continued

```
Ser Ala Ile Ser Trp Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Leu Phe Gly Leu Ala Leu Tyr Gly Glu Ala Phe Asp
                100                 105                 110

Val Trp Gly Gln Gly Thr Leu Val Thr Val Ser Ser
        115                 120

<210> SEQ ID NO 20
<211> LENGTH: 107
<212> TYPE: PRT
<213> ORGANISM: Artificial Sequence
<220> FEATURE:
<223> OTHER INFORMATION: 78-8D6 VL amino acid sequence - Artificial
      sequence translated from an isolated clone of an RNA display
      library

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Lys Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asn Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asn Ser Phe Pro Leu
                85                  90                  95

Thr Phe Gly Gln Gly Thr Lys Val Glu Ile Lys
            100                 105

<210> SEQ ID NO 21
<211> LENGTH: 124
<212> TYPE: PRT
<213> ORGANISM: Artificial Sequence
<220> FEATURE:
<223> OTHER INFORMATION: 78-8D7 VH amino acid sequence - Artificial
      sequence translated from an isolated clone of an RNA display
      library

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Val Met His Trp Val Arg Gln Ala Pro Gly Lys Gly Leu Glu Trp Val
            35                  40                  45

Ser Ala Ile Ser Trp Ser Gly Ala Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Leu Phe Gly Arg Ala Leu Tyr Gly Glu Ala Phe Asp
```

-continued

```
              100             105            110
Val Trp Gly Gln Gly Thr Leu Val Thr Val Ser Ser
        115             120
```

<210> SEQ ID NO 22
<211> LENGTH: 107
<212> TYPE: PRT
<213> ORGANISM: Artificial Sequence
<220> FEATURE:
<223> OTHER INFORMATION: 78-8D7 VL amino acid sequence - Artificial
      sequence translated from an isolated clone of an RNA display
      library

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Lys Asp Ile Ser Ile Tyr
            20                  25                  30

Leu Asn Trp Tyr Gln Gln Lys Pro Gly Lys Ala Pro Lys Leu Leu Ile
        35                  40                  45

Tyr Asp Ala Phe Asn Leu Glu Thr Gly Val Ser Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asn Ser Phe Pro Leu
                85                  90                  95

Thr Phe Gly Gln Gly Thr Lys Val Glu Ile Lys
            100             105
```

<210> SEQ ID NO 23
<211> LENGTH: 125
<212> TYPE: PRT
<213> ORGANISM: Artificial Sequence
<220> FEATURE:
<223> OTHER INFORMATION: 78-8D10 VH amino acid sequence - Artificial
      sequence translated from an isolated clone of an RNA display
      library

<400> SEQUENCE: 23

```
Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Val Met His Trp Val Arg Gln Ala Pro Gly Lys Gly Leu Glu Trp
        35                  40                  45

Val Ser Ala Ile Ser Trp Ser Gly Arg Gly Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Leu Phe Gly Leu Ala Leu Tyr Gly Glu Ala Phe
            100             105             110

Asp Val Trp Gly Gln Gly Thr Leu Val Thr Val Ser Ser
        115             120             125
```

<210> SEQ ID NO 24
<211> LENGTH: 107
<212> TYPE: PRT
<213> ORGANISM: Artificial Sequence -continued

```
<220> FEATURE:
<223> OTHER INFORMATION: 78-8D10 VL amino acid sequence - Artificial
      sequence translated from an isolated clone of an RNA display
      library

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Gln Ala Ser Lys Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asn Ser Phe Pro Leu
                85                  90                  95

Thr Phe Gly Gln Gly Thr Lys Val Glu Ile Lys
            100                 105

<210> SEQ ID NO 25
<211> LENGTH: 124
<212> TYPE: PRT
<213> ORGANISM: Artificial Sequence
<220> FEATURE:
<223> OTHER INFORMATION: 78-8D14 VH amino acid sequence - Artificial
      sequence translated from an isolated clone of an RNA display
      library

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met His Trp Val Arg Gln Ala Pro Gly Lys Gly Leu Glu Trp Val
        35                  40                  45

Ser Ala Ile Ser Trp Ser Gly Arg Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Leu Phe Gly Leu Ala Arg Tyr Gly Glu Ala Phe Asp
            100                 105                 110

Val Trp Gly Gln Gly Thr Leu Val Thr Val Ser Ser
        115                 120

<210> SEQ ID NO 26
<211> LENGTH: 107
<212> TYPE: PRT
<213> ORGANISM: Artificial Sequence
<220> FEATURE:
<223> OTHER INFORMATION: 78-8D14 VL amino acid sequence - Artificial
      sequence translated from an isolated clone of an RNA display
      library

<400> SEQUENCE: 26

Asp Ile Gln Met Thr Gln Ser Pro Ser Ser Leu Ser Ala Ser Val Gly
1               5                   10                  15
```

-continued

```
Asp Arg Val Thr Ile Thr Cys Gln Ala Ser Arg Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asn Ser Phe Pro Leu
                85                  90                  95

Thr Phe Gly Gln Gly Thr Lys Val Glu Ile Lys
            100                 105
```

<210> SEQ ID NO 27
<211> LENGTH: 124
<212> TYPE: PRT
<213> ORGANISM: Artificial Sequence
<220> FEATURE:
<223> OTHER INFORMATION: 78-8D22 VH amino acid sequence - Artificial
      sequence translated from an isolated clone of an RNA display
      library

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Val Met His Trp Val Arg Gln Ala Pro Gly Lys Gly Leu Glu Trp Val
            35                  40                  45

Ser Ala Ile Ser Trp Ser Gly Ser Gly Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Leu Phe Gly Leu Ala Arg Tyr Gly Glu Ala Phe Asp
                100                 105                 110

Val Trp Gly Gln Gly Thr Leu Val Thr Val Ser Ser
            115                 120
```

<210> SEQ ID NO 28
<211> LENGTH: 107
<212> TYPE: PRT
<213> ORGANISM: Artificial Sequence
<220> FEATURE:
<223> OTHER INFORMATION: 78-8D22 VL amino acid sequence - Artificial
      sequence translated from an isolated clone of an RNA display
      library

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Lys Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
```

```
65                  70                  75                  80

Glu Asp Ile Ala Thr Tyr Tyr Cys Gln Gln Phe Asn Ser Phe Ala Leu
                85                  90                  95

Thr Phe Gly Gln Gly Thr Lys Val Glu Ile Lys
            100                 105

<210> SEQ ID NO 29
<211> LENGTH: 120
<212> TYPE: PRT
<213> ORGANISM: Artificial Sequence
<220> FEATURE:
<223> OTHER INFORMATION: 78-13 VH amino acid sequence - Artificial
      sequence translated from an isolated clone of an RNA display
      library

<400> SEQUENCE: 29

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ser Ile Ile Ser Gly Ser Gly Arg Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asn Arg Asn Thr Tyr Gly Phe Asp Val Trp Gly Gln
            100                 105                 110

Gly Thr Leu Val Thr Val Ser Ser
        115                 120

<210> SEQ ID NO 30
<211> LENGTH: 107
<212> TYPE: PRT
<213> ORGANISM: Artificial Sequence
<220> FEATURE:
<223> OTHER INFORMATION: 78-13 VL amino acid sequence - Artificial
      sequence translated from an isolated clone of an RNA display
      library

<400> SEQUENCE: 30

Asp Ile Gln Met Thr Gln Ser Pro Ser Ser Leu Ser Ala Ser Val Gly
1                   5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Ser Ser Leu Pro Tyr
                85                  90                  95

Thr Phe Gly Gln Gly Thr Lys Val Glu Ile Lys
            100                 105

<210> SEQ ID NO 31
```

<211> LENGTH: 125
<212> TYPE: PRT
<213> ORGANISM: Artificial Sequence
<220> FEATURE:
<223> OTHER INFORMATION: 78-19 VH amino acid sequence - Artificial
      sequence translated from an isolated clone of an RNA display
      library

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met His Trp Val Arg Gln Ala Pro Gly Lys Gly Leu Glu Trp Val
        35                  40                  45

Ser Ala Ile Asn Gly Asn Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Tyr Thr His Arg Tyr Tyr Pro Gln Tyr Gly Phe
            100                 105                 110

Asp Val Trp Gly Gln Gly Thr Leu Val Thr Val Ser Ser
        115                 120                 125

<210> SEQ ID NO 32
<211> LENGTH: 107
<212> TYPE: PRT
<213> ORGANISM: Artificial Sequence
<220> FEATURE:
<223> OTHER INFORMATION: 78-19 VL amino acid sequence - Artificial
      sequence translated from an isolated clone of an RNA display
      library; X is any amino acid
<220> FEATURE:
<221> NAME/KEY: misc_feature
<222> LOCATION: (90)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Xaa Xaa Tyr Xaa Val Pro Tyr
                85                  90                  95

Thr Phe Gly Gln Gly Thr Lys Val Glu Ile Lys
            100                 105

<210> SEQ ID NO 33
<211> LENGTH: 125
<212> TYPE: PRT

```
<213> ORGANISM: Artificial Sequence
<220> FEATURE:
<223> OTHER INFORMATION: 78-24 VH amino acid sequence - Artificial
      sequence translated from an isolated clone of an RNA display
      library

<400> SEQUENCE: 33

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Ser Met His Trp Val Arg Gln Ala Pro Gly Lys Gly Leu Glu Trp
        35                  40                  45

Val Ser Gly Ile Ser Gly Ser Gly Gly Ser Thr Ser Tyr Ala Tyr Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Leu Met Ser Phe Asn Leu Thr Arg Thr Gly Gly Phe
            100                 105                 110

Asp Val Trp Gly Gln Gly Thr Leu Val Thr Val Ser Ser
            115                 120                 125

<210> SEQ ID NO 34
<211> LENGTH: 107
<212> TYPE: PRT
<213> ORGANISM: Artificial Sequence
<220> FEATURE:
<223> OTHER INFORMATION: 78-24 VL amino acid sequence - Artificial
      sequence translated from an isolated clone of an RNA display
      library

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Trp Pro Trp
                85                  90                  95

Thr Phe Gly Gln Gly Thr Lys Val Glu Ile Lys
            100                 105

<210> SEQ ID NO 35
<211> LENGTH: 124
<212> TYPE: PRT
<213> ORGANISM: Artificial Sequence
<220> FEATURE:
<223> OTHER INFORMATION: 78-24D1 VH amino acid sequence - Artificial
      sequence translated from an isolated clone of an RNA display
      library

<400> SEQUENCE: 35

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Thr Ser Tyr
        20                  25                  30

Ser Met His Trp Val Arg Gln Ala Pro Gly Lys Gly Leu Glu Trp Val
        35                  40                  45

Ser Gly Ile Ser Gly Ser Gly Arg Ser Thr Ser Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Met Ala Phe Asn Leu Thr Arg Ala Gly Gly Phe Asp
                100                 105                 110

Val Trp Gly Gln Gly Thr Leu Val Thr Val Ser Ser
        115                 120
```

```
<210> SEQ ID NO 36
<211> LENGTH: 124
<212> TYPE: PRT
<213> ORGANISM: Artificial Sequence
<220> FEATURE:
<223> OTHER INFORMATION: 78-24D1V VH amino acid sequence - Artificial
      sequence translated from an isolated clone of an RNA display
      library

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
        20                  25                  30

Ser Met His Trp Val Arg Gln Ala Pro Gly Lys Gly Leu Glu Trp Val
        35                  40                  45

Ser Gly Ile Ser Gly Ser Gly Arg Ser Thr Ser Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Met Ala Phe Asn Leu Val Arg Ala Gly Gly Phe Asp
                100                 105                 110

Val Trp Gly Gln Gly Thr Leu Val Thr Val Ser Ser
        115                 120
```

```
<210> SEQ ID NO 37
<211> LENGTH: 107
<212> TYPE: PRT
<213> ORGANISM: Artificial Sequence
<220> FEATURE:
<223> OTHER INFORMATION: 78-24D1 VL amino acid sequence - Artificial
      sequence translated from an isolated clone of an RNA display
      library

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Phe
        20                  25                  30

Leu Asn Trp Tyr Gln Gln Lys Pro Gly Lys Ala Pro Lys Leu Leu Ile
        35                  40                  45
```

-continued

```
Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Trp Pro Trp
                85                  90                  95

Thr Phe Gly Gln Gly Thr Lys Val Glu Ile Lys
            100                 105

<210> SEQ ID NO 38
<211> LENGTH: 124
<212> TYPE: PRT
<213> ORGANISM: Artificial Sequence
<220> FEATURE:
<223> OTHER INFORMATION: 78-24D4 VH amino acid sequence - Artificial
      sequence translated from an isolated clone of an RNA display
      library

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met His Trp Val Arg Gln Ala Pro Gly Lys Gly Leu Glu Trp Val
        35                  40                  45

Ser Gly Ile Ser Phe Ser Gly Arg Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Leu Met Ser Phe Asn Leu Thr Arg Thr Ser Trp Phe Asp
            100                 105                 110

Val Trp Gly Gln Gly Thr Leu Val Thr Val Ser Ser
            115                 120

<210> SEQ ID NO 39
<211> LENGTH: 107
<212> TYPE: PRT
<213> ORGANISM: Artificial Sequence
<220> FEATURE:
<223> OTHER INFORMATION: 78-24D4 VL amino acid sequence - Artificial
      sequence translated from an isolated clone of an RNA display
      library

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Trp Pro Trp
                85                  90                  95

Thr Phe Gly Gln Gly Thr Lys Val Glu Ile Lys
```

```
                  100                 105
```

<210> SEQ ID NO 40
<211> LENGTH: 124
<212> TYPE: PRT
<213> ORGANISM: Artificial Sequence
<220> FEATURE:
<223> OTHER INFORMATION: 78-24D8 VH amino acid sequence - Artificial
      sequence translated from an isolated clone of an RNA display
      library

<400> SEQUENCE: 40

Glu Val Gln Leu Val Lys Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met His Trp Val Arg Gln Ala Pro Gly Lys Gly Leu Glu Trp Val
        35                  40                  45

Ser Gly Ile Ser Gly Ser Gly Arg Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Met Ala Phe Asn Leu Thr Arg Thr Gly Gly Phe Asp
            100                 105                 110

Val Trp Gly Gln Gly Thr Leu Val Thr Val Ser Ser
        115                 120

<210> SEQ ID NO 41
<211> LENGTH: 107
<212> TYPE: PRT
<213> ORGANISM: Artificial Sequence
<220> FEATURE:
<223> OTHER INFORMATION: 78-24D8 VL amino acid sequence - Artificial
      sequence translated from an isolated clone of an RNA display
      library

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Asn Ser Leu Gln Pro
65                  70                  75                  80

Glu Asp Ile Ala Thr Tyr Tyr Cys Gln Gln Gly Asp Ala Trp Pro Trp
                85                  90                  95

Thr Phe Gly Gln Gly Thr Lys Val Glu Ile Lys
            100                 105

<210> SEQ ID NO 42
<211> LENGTH: 124
<212> TYPE: PRT
<213> ORGANISM: Artificial Sequence
<220> FEATURE:
<223> OTHER INFORMATION: 78-24D9 VH amino acid sequence - Artificial
      sequence translated from an isolated clone of an RNA display library

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ser Met His Trp Val Arg Gln Ala Pro Gly Lys Gly Leu Glu Trp Val
        35                  40                  45

Ser Gly Ile Ser Gly Trp Gly Gly Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Leu Met Ser Phe Asn Leu Thr Arg Thr Gly Trp Phe Asp
            100                 105                 110

Val Trp Gly Gln Gly Thr Leu Val Thr Val Ser Ser
        115                 120

<210> SEQ ID NO 43
<211> LENGTH: 107
<212> TYPE: PRT
<213> ORGANISM: Artificial Sequence
<220> FEATURE:
<223> OTHER INFORMATION: 78-24D9 VL amino acid sequence - Artificial
      sequence translated from an isolated clone of an RNA display
      library

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ala Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Ala Trp Pro Trp
                85                  90                  95

Thr Phe Gly Gln Gly Thr Lys Val Glu Ile Lys
            100                 105

<210> SEQ ID NO 44
<211> LENGTH: 124
<212> TYPE: PRT
<213> ORGANISM: Artificial Sequence
<220> FEATURE:
<223> OTHER INFORMATION: 78-24D12 VH amino acid sequence - Artificial
      sequence translated from an isolated clone of an RNA display
      library

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ser Met His Trp Val Arg Gln Ala Pro Gly Lys Gly Leu Glu Trp Val
        35                  40                  45

Ser Gly Ile Ser Gly Ser Gly Leu Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Met Ala Phe Asn Leu Thr Arg Thr Gly Gly Phe Asp
            100                 105                 110

Val Trp Gly Gln Gly Thr Leu Val Thr Val Ser Ser
        115                 120
```

```
<210> SEQ ID NO 45
<211> LENGTH: 107
<212> TYPE: PRT
<213> ORGANISM: Artificial Sequence
<220> FEATURE:
<223> OTHER INFORMATION: 78-24D12 VL amino acid sequence - Artificial
      sequence translated from an isolated clone of an RNA display
      library

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Gln Ala Ser His Asp Ile Leu Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly His Ala Trp Leu Trp
                85                  90                  95

Thr Phe Gly Gln Gly Thr Lys Val Glu Ile Lys
            100                 105
```

```
<210> SEQ ID NO 46
<211> LENGTH: 124
<212> TYPE: PRT
<213> ORGANISM: Artificial Sequence
<220> FEATURE:
<223> OTHER INFORMATION: 78-24D14 VH amino acid sequence - Artificial
      sequence translated from an isolated clone of an RNA display
      library

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Phe Ser Tyr
            20                  25                  30

Ser Met His Trp Val Arg Gln Ala Pro Gly Lys Gly Leu Glu Trp Val
        35                  40                  45

Ser Gly Ile Ser Gly Ser Gly Trp Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                        85                  90                  95

Val Arg Asp Leu Met Ser Phe Asn Met Thr Arg Ala Gly Gly Phe Asp
            100                 105                 110

Val Trp Gly Gln Gly Thr Leu Val Thr Val Ser Ser
        115                 120

<210> SEQ ID NO 47
<211> LENGTH: 107
<212> TYPE: PRT
<213> ORGANISM: Artificial Sequence
<220> FEATURE:
<223> OTHER INFORMATION: 78-24D14 VL amino acid sequence - Artificial
      sequence translated from an isolated clone of an RNA display
      library

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Trp Pro Trp
                85                  90                  95

Thr Phe Gly Gln Gly Thr Lys Val Glu Ile Lys
            100                 105

<210> SEQ ID NO 48
<211> LENGTH: 124
<212> TYPE: PRT
<213> ORGANISM: Artificial Sequence
<220> FEATURE:
<223> OTHER INFORMATION: 78-24D17 VH amino acid sequence - Artificial
      sequence translated from an isolated clone of an RNA display
      library

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ser Met His Trp Val Arg Gln Ala Pro Gly Lys Gly Leu Glu Trp Val
        35                  40                  45

Ser Gly Ile Ser Gly Ser Gly Gly Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Leu Met Ser Phe Asn Leu Thr Arg Thr Ser Trp Phe Asp
            100                 105                 110

Val Trp Gly Gln Gly Thr Leu Val Thr Val Ser Ser
        115                 120

<210> SEQ ID NO 49
```

<211> LENGTH: 124
<212> TYPE: PRT
<213> ORGANISM: Artificial Sequence
<220> FEATURE:
<223> OTHER INFORMATION: 78-24D17V VH amino acid sequence - Artificial
      sequence translated from an isolated clone of an RNA display
      library

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ser Met His Trp Val Arg Gln Ala Pro Gly Lys Gly Leu Glu Trp Val
        35                  40                  45

Ser Gly Ile Ser Gly Ser Gly Gly Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Leu Met Ser Phe Asn Leu Val Arg Thr Ser Trp Phe Asp
            100                 105                 110

Val Trp Gly Gln Gly Thr Leu Val Thr Val Ser Ser
        115                 120

<210> SEQ ID NO 50
<211> LENGTH: 107
<212> TYPE: PRT
<213> ORGANISM: Artificial Sequence
<220> FEATURE:
<223> OTHER INFORMATION: 78-24D17 VL amino acid sequence - Artificial
      sequence translated from an isolated clone of an RNA display
      library

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ala Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Trp Pro Trp
                85                  90                  95

Thr Phe Gly Gln Gly Thr Lys Val Glu Ile Lys
            100                 105

<210> SEQ ID NO 51
<211> LENGTH: 124
<212> TYPE: PRT
<213> ORGANISM: Artificial Sequence
<220> FEATURE:
<223> OTHER INFORMATION: 78-24D22 VH amino acid sequence - Artificial
      sequence translated from an isolated clone of an RNA display
      library

<400> SEQUENCE: 51

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Ser Tyr
            20                  25                  30

Ser Met His Trp Val Arg Gln Ala Pro Gly Lys Gly Leu Glu Trp Val
            35                  40                  45

Ser Gly Ile Ser Gly Ser Gly Trp Ser Thr Ser Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Met Ala Phe Asn Leu Thr Arg Ala Gly Gly Phe Asp
                100                 105                 110

Val Trp Gly Gln Gly Thr Leu Val Thr Val Ser Ser
            115                 120
```

<210> SEQ ID NO 52
<211> LENGTH: 124
<212> TYPE: PRT
<213> ORGANISM: Artificial Sequence
<220> FEATURE:
<223> OTHER INFORMATION: 78-24D22V VH amino acid sequence - Artificial
      sequence translated from an isolated clone of an RNA display
      library

<400> SEQUENCE: 52

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Ser Tyr
            20                  25                  30

Ser Met His Trp Val Arg Gln Ala Pro Gly Lys Gly Leu Glu Trp Val
            35                  40                  45

Ser Gly Ile Ser Gly Ser Gly Trp Ser Thr Ser Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Met Ala Phe Asn Leu Val Arg Ala Gly Gly Phe Asp
                100                 105                 110

Val Trp Gly Gln Gly Thr Leu Val Thr Val Ser Ser
            115                 120
```

<210> SEQ ID NO 53
<211> LENGTH: 107
<212> TYPE: PRT
<213> ORGANISM: Artificial Sequence
<220> FEATURE:
<223> OTHER INFORMATION: 78-24D22 VL amino acid sequence - Artificial
      sequence translated from an isolated clone of an RNA display
      library

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
```

-continued

```
                35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Trp Pro Trp
                85                  90                  95

Thr Phe Gly Gln Gly Thr Lys Val Glu Ile Lys
            100                 105

<210> SEQ ID NO 54
<211> LENGTH: 121
<212> TYPE: PRT
<213> ORGANISM: Artificial Sequence
<220> FEATURE:
<223> OTHER INFORMATION: 78-28 VH amino acid sequence - Artificial
      sequence translated from an isolated clone of an RNA display
      library

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Tyr Met His Trp Val Arg Gln Ala Pro Gly Lys Gly Leu Glu Trp Val
            35                  40                  45

Ser Ala Ile Tyr Gly Asn Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Ala Arg His Gln Val Gly Phe Asp Val Trp Gly
            100                 105                 110

Gln Gly Thr Leu Val Thr Val Ser Ser
        115                 120

<210> SEQ ID NO 55
<211> LENGTH: 107
<212> TYPE: PRT
<213> ORGANISM: Artificial Sequence
<220> FEATURE:
<223> OTHER INFORMATION: 78-28 VL amino acid sequence - Artificial
      sequence translated from an isolated clone of an RNA display
      library

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Gln Ala Ser Leu Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Tyr Thr Val Pro Leu
                85                  90                  95
```

-continued

```
Thr Phe Gly Gln Gly Thr Lys Val Glu Ile Lys
            100                 105

<210> SEQ ID NO 56
<211> LENGTH: 125
<212> TYPE: PRT
<213> ORGANISM: Artificial Sequence
<220> FEATURE:
<223> OTHER INFORMATION: 78-36 VH amino acid sequence - Artificial
      sequence translated from an isolated clone of an RNA display
      library

<400> SEQUENCE: 56

Met Glu Val Gln Leu Val Glu Ser Gly Gly Gly Leu Val Gln Pro Gly
1               5                   10                  15

Gly Ser Leu Arg Leu Ser Cys Val Ala Ser Gly Phe Thr Phe Ser Ser
            20                  25                  30

Tyr Tyr Met His Trp Val Arg Gln Ala Pro Gly Lys Gly Leu Glu Trp
        35                  40                  45

Val Ser Ala Ile Ser Gly Ser Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Gln Val Gly Lys Ser Ser Phe Gly Glu Ala Phe
            100                 105                 110

Asp Val Trp Gly Gln Gly Thr Leu Val Thr Val Ser Ser
        115                 120                 125

<210> SEQ ID NO 57
<211> LENGTH: 107
<212> TYPE: PRT
<213> ORGANISM: Artificial Sequence
<220> FEATURE:
<223> OTHER INFORMATION: 78-36 VL amino acid sequence - Artificial
      sequence translated from an isolated clone of an RNA display
      library

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Thr Ser Phe Pro Tyr
                85                  90                  95

Thr Phe Gly Gln Gly Thr Lys Val Glu Ile Lys
            100                 105

<210> SEQ ID NO 58
<211> LENGTH: 123
<212> TYPE: PRT
<213> ORGANISM: Artificial Sequence
<220> FEATURE:
```

-continued

<223> OTHER INFORMATION: 78-39 VH amino acid sequence - Artificial
      sequence translated from an isolated clone of an RNA display
      library

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Ala Met His Trp Val Arg Gln Ala Pro Gly Lys Gly Leu Glu Trp Val
        35                  40                  45

Ser Ala Ile Ser Trp Ser Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Arg Pro Thr Tyr Lys Met Ser Ile Gly Phe Asp Val
            100                 105                 110

Trp Gly Gln Gly Thr Leu Val Thr Val Ser Ser
        115                 120

<210> SEQ ID NO 59
<211> LENGTH: 107
<212> TYPE: PRT
<213> ORGANISM: Artificial Sequence
<220> FEATURE:
<223> OTHER INFORMATION: 78-39 VL amino acid sequence - Artificial
      sequence translated from an isolated clone of an RNA display
      library

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gln Gly Thr Lys Val Glu Ile Lys
            100                 105

<210> SEQ ID NO 60
<211> LENGTH: 454
<212> TYPE: PRT
<213> ORGANISM: Artificial Sequence
<220> FEATURE:
<223> OTHER INFORMATION: 78-8D2 HC amino acid sequence - Artificial
      sequence translated from an isolated clone of an RNA display
      library

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

-continued

```
                  20              25              30
Val Met His Trp Val Arg Gln Ala Pro Gly Lys Gly Leu Glu Trp Val
         35              40              45

Ser Ala Ile Thr Trp Ser Gly Arg Gly Thr Tyr Tyr Ala Asp Ser Val
     50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
             85              90              95

Ala Arg Gly Arg Leu Phe Gly Leu Ala Leu Tyr Gly Glu Ala Phe Asp
            100             105             110

Val Trp Gly Gln Gly Thr Leu Val Thr Val Ser Ser Ala Ser Thr Lys
        115             120             125

Gly Pro Ser Val Phe Pro Leu Ala Pro Ser Ser Lys Ser Thr Ser Gly
        130             135             140

Gly Thr Ala Ala Leu Gly Cys Leu Val Lys Asp Tyr Phe Pro Glu Pro
145             150             155             160

Val Thr Val Ser Trp Asn Ser Gly Ala Leu Thr Ser Gly Val His Thr
            165             170             175

Phe Pro Ala Val Leu Gln Ser Ser Gly Leu Tyr Ser Leu Ser Ser Val
            180             185             190

Val Thr Val Pro Ser Ser Ser Leu Gly Thr Gln Thr Tyr Ile Cys Asn
            195             200             205

Val Asn His Lys Pro Ser Asn Thr Lys Val Asp Lys Lys Val Glu Pro
    210             215             220

Lys Ser Cys Asp Lys Thr His Thr Cys Pro Pro Cys Pro Ala Pro Glu
225             230             235             240

Leu Leu Gly Gly Pro Ser Val Phe Leu Phe Pro Pro Lys Pro Lys Asp
            245             250             255

Thr Leu Met Ile Ser Arg Thr Pro Glu Val Thr Cys Val Val Val Asp
            260             265             270

Val Ser His Glu Asp Pro Glu Val Lys Phe Asn Trp Tyr Val Asp Gly
        275             280             285

Val Glu Val His Asn Ala Lys Thr Lys Pro Arg Glu Glu Gln Tyr Asn
    290             295             300

Ser Thr Tyr Arg Val Val Ser Val Leu Thr Val Leu His Gln Asp Trp
305             310             315             320

Leu Asn Gly Lys Glu Tyr Lys Cys Lys Val Ser Asn Lys Ala Leu Pro
            325             330             335

Ala Pro Ile Glu Lys Thr Ile Ser Lys Ala Lys Gly Gln Pro Arg Glu
            340             345             350

Pro Gln Val Tyr Thr Leu Pro Pro Ser Arg Asp Glu Leu Thr Lys Asn
            355             360             365

Gln Val Ser Leu Thr Cys Leu Val Lys Gly Phe Tyr Pro Ser Asp Ile
    370             375             380

Ala Val Glu Trp Glu Ser Asn Gly Gln Pro Glu Asn Asn Tyr Lys Thr
385             390             395             400

Thr Pro Pro Val Leu Asp Ser Asp Gly Ser Phe Phe Leu Tyr Ser Lys
            405             410             415

Leu Thr Val Asp Lys Ser Arg Trp Gln Gln Gly Asn Val Phe Ser Cys
            420             425             430

Ser Val Met His Glu Ala Leu His Asn His Tyr Thr Gln Lys Ser Leu
            435             440             445
```

-continued

```
Ser Leu Ser Pro Gly Lys
    450

<210> SEQ ID NO 61
<211> LENGTH: 454
<212> TYPE: PRT
<213> ORGANISM: Artificial Sequence
<220> FEATURE:
<223> OTHER INFORMATION: 78-8D4 HC amino acid sequence - Artificial
      sequence translated from an isolated clone of an RNA display
      library

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met His Trp Val Arg Gln Ala Pro Gly Lys Gly Leu Glu Trp Val
        35                  40                  45

Ser Ala Ile Thr Trp Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Arg Leu Phe Gly Leu Val Arg Tyr Gly Glu Ala Phe Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335
```

-continued

```
Ala Pro Ile Glu Lys Thr Ile Ser Lys Ala Lys Gly Gln Pro Arg Glu
            340             345             350

Pro Gln Val Tyr Thr Leu Pro Pro Ser Arg Asp Glu Leu Thr Lys Asn
            355             360             365

Gln Val Ser Leu Thr Cys Leu Val Lys Gly Phe Tyr Pro Ser Asp Ile
            370             375             380

Ala Val Glu Trp Glu Ser Asn Gly Gln Pro Glu Asn Asn Tyr Lys Thr
385             390             395             400

Thr Pro Pro Val Leu Asp Ser Asp Gly Ser Phe Phe Leu Tyr Ser Lys
                405             410             415

Leu Thr Val Asp Lys Ser Arg Trp Gln Gln Gly Asn Val Phe Ser Cys
                420             425             430

Ser Val Met His Glu Ala Leu His Asn His Tyr Thr Gln Lys Ser Leu
            435             440             445

Ser Leu Ser Pro Gly Lys
    450
```

```
<210> SEQ ID NO 62
<211> LENGTH: 454
<212> TYPE: PRT
<213> ORGANISM: Artificial Sequence
<220> FEATURE:
<223> OTHER INFORMATION: 78-8D22 HC amino acid sequence - Artificial
      sequence translated from an isolated clone of an RNA display
      library

<400> SEQUENCE: 62
```

```
Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Ser Tyr
            20              25              30

Val Met His Trp Val Arg Gln Ala Pro Gly Lys Gly Leu Glu Trp Val
            35              40              45

Ser Ala Ile Ser Trp Ser Gly Ser Gly Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Gly Arg Leu Phe Gly Leu Ala Arg Tyr Gly Glu Ala Phe Asp
            100             105             110

Val Trp Gly Gln Gly Thr Leu Val Thr Val Ser Ser Ala Ser Thr Lys
            115             120             125

Gly Pro Ser Val Phe Pro Leu Ala Pro Ser Ser Lys Ser Thr Ser Gly
            130             135             140

Gly Thr Ala Ala Leu Gly Cys Leu Val Lys Asp Tyr Phe Pro Glu Pro
145             150             155             160

Val Thr Val Ser Trp Asn Ser Gly Ala Leu Thr Ser Gly Val His Thr
                165             170             175

Phe Pro Ala Val Leu Gln Ser Ser Gly Leu Tyr Ser Leu Ser Ser Val
            180             185             190

Val Thr Val Pro Ser Ser Ser Leu Gly Thr Gln Thr Tyr Ile Cys Asn
            195             200             205

Val Asn His Lys Pro Ser Asn Thr Lys Val Asp Lys Lys Val Glu Pro
    210             215             220

Lys Ser Cys Asp Lys Thr His Thr Cys Pro Pro Cys Pro Ala Pro Glu
```

-continued

```
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
        435                 440                 445

Ser Leu Ser Pro Gly Lys
        450
```

```
<210> SEQ ID NO 63
<211> LENGTH: 214
<212> TYPE: PRT
<213> ORGANISM: Artificial Sequence
<220> FEATURE:
<223> OTHER INFORMATION: 78-8 LC amino acid sequence - Artificial
      sequence translated from an isolated clone of an RNA display
      library

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Gln Ala Ser Lys Asp Ile Ser Asn Tyr
                20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asn Ser Phe Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125
```

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 64
<211> LENGTH: 454
<212> TYPE: PRT
<213> ORGANISM: Artificial Sequence
<220> FEATURE:
<223> OTHER INFORMATION: 78-24D1V HC amino acid sequence - Artificial
      sequence translated from an isolated clone of an RNA display
      library

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Met His Trp Val Arg Gln Ala Pro Gly Lys Gly Leu Glu Trp Val
            35                  40                  45

Ser Gly Ile Ser Gly Ser Gly Arg Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Met Ala Phe Asn Leu Val Arg Ala Gly Gly Phe Asp
            100                 105                 110

Val Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255
```

```
Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
        450
```

```
<210> SEQ ID NO 65
<211> LENGTH: 454
<212> TYPE: PRT
<213> ORGANISM: Artificial Sequence
<220> FEATURE:
<223> OTHER INFORMATION: 78-24D17V HC amino acid sequence - Artificial
      sequence translated from an isolated clone of an RNA display
      library

<400> SEQUENCE: 65
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ser Met His Trp Val Arg Gln Ala Pro Gly Lys Gly Leu Glu Trp Val
        35                  40                  45

Ser Gly Ile Ser Gly Ser Gly Gly Ser Thr Ser Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Leu Met Ser Phe Asn Leu Val Arg Thr Ser Trp Phe Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
```

-continued

```
145                150                155                160

Val Thr Val Ser Trp Asn Ser Gly Ala Leu Thr Ser Gly Val His Thr
                165                170                175

Phe Pro Ala Val Leu Gln Ser Ser Gly Leu Tyr Ser Leu Ser Ser Val
                180                185                190

Val Thr Val Pro Ser Ser Ser Leu Gly Thr Gln Thr Tyr Ile Cys Asn
                195                200                205

Val Asn His Lys Pro Ser Asn Thr Lys Val Asp Lys Lys Val Glu Pro
    210                215                220

Lys Ser Cys Asp Lys Thr His Thr Cys Pro Pro Cys Pro Ala Pro Glu
225                230                235                240

Leu Leu Gly Gly Pro Ser Val Phe Leu Phe Pro Pro Lys Pro Lys Asp
                245                250                255

Thr Leu Met Ile Ser Arg Thr Pro Glu Val Thr Cys Val Val Val Asp
                260                265                270

Val Ser His Glu Asp Pro Glu Val Lys Phe Asn Trp Tyr Val Asp Gly
                275                280                285

Val Glu Val His Asn Ala Lys Thr Lys Pro Arg Glu Glu Gln Tyr Asn
    290                295                300

Ser Thr Tyr Arg Val Val Ser Val Leu Thr Val Leu His Gln Asp Trp
305                310                315                320

Leu Asn Gly Lys Glu Tyr Lys Cys Lys Val Ser Asn Lys Ala Leu Pro
                325                330                335

Ala Pro Ile Glu Lys Thr Ile Ser Lys Ala Lys Gly Gln Pro Arg Glu
                340                345                350

Pro Gln Val Tyr Thr Leu Pro Pro Ser Arg Asp Glu Leu Thr Lys Asn
                355                360                365

Gln Val Ser Leu Thr Cys Leu Val Lys Gly Phe Tyr Pro Ser Asp Ile
    370                375                380

Ala Val Glu Trp Glu Ser Asn Gly Gln Pro Glu Asn Asn Tyr Lys Thr
385                390                395                400

Thr Pro Pro Val Leu Asp Ser Asp Gly Ser Phe Phe Leu Tyr Ser Lys
                405                410                415

Leu Thr Val Asp Lys Ser Arg Trp Gln Gln Gly Asn Val Phe Ser Cys
                420                425                430

Ser Val Met His Glu Ala Leu His Asn His Tyr Thr Gln Lys Ser Leu
    435                440                445

Ser Leu Ser Pro Gly Lys
    450

<210> SEQ ID NO 66
<211> LENGTH: 454
<212> TYPE: PRT
<213> ORGANISM: Artificial Sequence
<220> FEATURE:
<223> OTHER INFORMATION: 78-24D22V HC amino acid sequence - Artificial
      sequence translated from an isolated clone of an RNA display
      library

<400> SEQUENCE: 66

Glu Val Gln Leu Val Glu Ser Gly Gly Gly Leu Val Gln Pro Gly Gly
1                5                10                15

Ser Leu Arg Leu Ser Cys Ala Ala Ser Gly Phe Thr Phe Pro Ser Tyr
                20                25                30

Ser Met His Trp Val Arg Gln Ala Pro Gly Lys Gly Leu Glu Trp Val
                35                40                45
```

```
Ser Gly Ile Ser Gly Ser Gly Trp Ser Thr Ser Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Asp Leu Met Ala Phe Asn Leu Val Arg Ala Gly Gly Phe Asp
            100             105             110

Val Trp Gly Gln Gly Thr Leu Val Thr Val Ser Ser Ala Ser Thr Lys
        115             120             125

Gly Pro Ser Val Phe Pro Leu Ala Pro Ser Ser Lys Ser Thr Ser Gly
    130             135             140

Gly Thr Ala Ala Leu Gly Cys Leu Val Lys Asp Tyr Phe Pro Glu Pro
145             150             155             160

Val Thr Val Ser Trp Asn Ser Gly Ala Leu Thr Ser Gly Val His Thr
            165             170             175

Phe Pro Ala Val Leu Gln Ser Ser Gly Leu Tyr Ser Leu Ser Ser Val
            180             185             190

Val Thr Val Pro Ser Ser Ser Leu Gly Thr Gln Thr Tyr Ile Cys Asn
        195             200             205

Val Asn His Lys Pro Ser Asn Thr Lys Val Asp Lys Lys Val Glu Pro
    210             215             220

Lys Ser Cys Asp Lys Thr His Thr Cys Pro Pro Cys Pro Ala Pro Glu
225             230             235             240

Leu Leu Gly Gly Pro Ser Val Phe Leu Phe Pro Pro Lys Pro Lys Asp
            245             250             255

Thr Leu Met Ile Ser Arg Thr Pro Glu Val Thr Cys Val Val Val Asp
            260             265             270

Val Ser His Glu Asp Pro Glu Val Lys Phe Asn Trp Tyr Val Asp Gly
        275             280             285

Val Glu Val His Asn Ala Lys Thr Lys Pro Arg Glu Glu Gln Tyr Asn
    290             295             300

Ser Thr Tyr Arg Val Val Ser Val Leu Thr Val Leu His Gln Asp Trp
305             310             315             320

Leu Asn Gly Lys Glu Tyr Lys Cys Lys Val Ser Asn Lys Ala Leu Pro
            325             330             335

Ala Pro Ile Glu Lys Thr Ile Ser Lys Ala Lys Gly Gln Pro Arg Glu
            340             345             350

Pro Gln Val Tyr Thr Leu Pro Pro Ser Arg Asp Glu Leu Thr Lys Asn
        355             360             365

Gln Val Ser Leu Thr Cys Leu Val Lys Gly Phe Tyr Pro Ser Asp Ile
    370             375             380

Ala Val Glu Trp Glu Ser Asn Gly Gln Pro Glu Asn Asn Tyr Lys Thr
385             390             395             400

Thr Pro Pro Val Leu Asp Ser Asp Gly Ser Phe Phe Leu Tyr Ser Lys
            405             410             415

Leu Thr Val Asp Lys Ser Arg Trp Gln Gln Gly Asn Val Phe Ser Cys
            420             425             430

Ser Val Met His Glu Ala Leu His Asn His Tyr Thr Gln Lys Ser Leu
        435             440             445

Ser Leu Ser Pro Gly Lys
    450
```

<210> SEQ ID NO 67
<211> LENGTH: 214
<212> TYPE: PRT
<213> ORGANISM: Artificial Sequence
<220> FEATURE:
<223> OTHER INFORMATION: 78-24 LC amino acid sequence - Artificial
      sequence translated from an isolated clone of an RNA display
      library

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 68
<211> LENGTH: 454
<212> TYPE: PRT
<213> ORGANISM: Artificial Sequence
<220> FEATURE:
<223> OTHER INFORMATION: CTLA4-7 HC amino acid sequence - Artificial
      sequence translated from an isolated clone of an RNA display
      library

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Met His Trp Val Arg Gln Ala Pro Gly Lys Gly Leu Glu Trp Val
        35                  40                  45

Ser Gly Ile Ser Gly Ser Gly Arg Ser Thr Ser Tyr Ala Asp Ser Val
    50                  55                  60

Lys Gly Arg Phe Thr Ile Ser Arg Asp Asn Ser Lys Asn Thr Leu Tyr

-continued

```
65                    70                    75                    80

Leu Gln Met Asn Ser Leu Arg Ala Glu Asp Thr Ala Val Tyr Tyr Cys
             85                    90                    95

Ala Arg Asp Leu Met Ala Phe Asn Leu Val Arg Ala Gly Gly Phe Asp
             100                   105                   110

Val Trp Gly Gln Gly Thr Leu Val Thr Val Ser Ser Ala Ser Thr Lys
             115                   120                   125

Gly Pro Ser Val Phe Pro Leu Ala Pro Ser Ser Lys Ser Thr Ser Gly
         130                   135                   140

Gly Thr Ala Ala Leu Gly Cys Leu Val Lys Asp Tyr Phe Pro Glu Pro
145                   150                   155                   160

Val Thr Val Ser Trp Asn Ser Gly Ala Leu Thr Ser Gly Val His Thr
             165                   170                   175

Phe Pro Ala Val Leu Gln Ser Ser Gly Leu Tyr Ser Leu Ser Ser Val
             180                   185                   190

Val Thr Val Pro Ser Ser Ser Leu Gly Thr Gln Thr Tyr Ile Cys Asn
             195                   200                   205

Val Asn His Lys Pro Ser Asn Thr Lys Val Asp Lys Lys Val Glu Pro
         210                   215                   220

Lys Ser Cys Asp Lys Thr His Thr Cys Pro Pro Cys Pro Ala Pro Glu
225                   230                   235                   240

Leu Leu Gly Gly Pro Ser Val Phe Leu Phe Pro Pro Lys Pro Lys Asp
             245                   250                   255

Thr Leu Met Ile Ser Arg Thr Pro Glu Val Thr Cys Val Val Val Asp
             260                   265                   270

Val Ser His Glu Asp Pro Glu Val Lys Phe Asn Trp Tyr Val Asp Gly
             275                   280                   285

Val Glu Val His Asn Ala Lys Thr Lys Pro Arg Glu Glu Gln Tyr Asn
         290                   295                   300

Ser Thr Tyr Arg Val Val Ser Val Leu Thr Val Leu His Gln Asp Trp
305                   310                   315                   320

Leu Asn Gly Lys Glu Tyr Lys Cys Lys Val Ser Asn Lys Ala Leu Pro
             325                   330                   335

Ala Pro Ile Glu Lys Thr Ile Ser Lys Ala Lys Gly Gln Pro Arg Glu
             340                   345                   350

Pro Gln Val Tyr Thr Leu Pro Pro Ser Arg Asp Glu Leu Thr Lys Asn
             355                   360                   365

Gln Val Ser Leu Thr Cys Leu Val Lys Gly Phe Tyr Pro Ser Asp Ile
         370                   375                   380

Ala Val Glu Trp Glu Ser Asn Gly Gln Pro Glu Asn Asn Tyr Lys Thr
385                   390                   395                   400

Thr Pro Pro Val Leu Asp Ser Asp Gly Ser Phe Phe Leu Tyr Ser Lys
             405                   410                   415

Leu Thr Val Asp Lys Ser Arg Trp Gln Gln Gly Asn Val Phe Ser Cys
             420                   425                   430

Ser Val Met His Glu Ala Leu His Asn His Tyr Thr Gln Lys Ser Leu
         435                   440                   445

Ser Leu Ser Pro Gly Lys
    450
```

```
<210> SEQ ID NO 69
<211> LENGTH: 214
<212> TYPE: PRT
<213> ORGANISM: Artificial Sequence
```

```
<220> FEATURE:
<223> OTHER INFORMATION: CTLA4-7 LC amino acid sequence - Artificial
      sequence translated from an isolated clone of an RNA display
      library

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 70
<211> LENGTH: 454
<212> TYPE: PRT
<213> ORGANISM: Artificial Sequence
<220> FEATURE:
<223> OTHER INFORMATION: CTLA4-8 HC amino acid sequence - Artificial
      sequence translated from an isolated clone of an RNA display
      library

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ser Met His Trp Val Arg Gln Ala Pro Gly Lys Gly Leu Glu Trp Val
            35                  40                  45

Ser Gly Ile Ser Gly Ser Gly Gly Ser Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Tyr Leu Met Ser Phe Asn Leu Val Arg Thr Ser Trp Phe Asp
            100             105             110

Val Trp Gly Gln Gly Thr Leu Val Thr Val Ser Ser Ala Ser Thr Lys
            115             120             125

Gly Pro Ser Val Phe Pro Leu Ala Pro Ser Ser Lys Ser Thr Ser Gly
            130             135             140

Gly Thr Ala Ala Leu Gly Cys Leu Val Lys Asp Tyr Phe Pro Glu Pro
145             150             155             160

Val Thr Val Ser Trp Asn Ser Gly Ala Leu Thr Ser Gly Val His Thr
            165             170             175

Phe Pro Ala Val Leu Gln Ser Ser Gly Leu Tyr Ser Leu Ser Ser Val
            180             185             190

Val Thr Val Pro Ser Ser Ser Leu Gly Thr Gln Thr Tyr Ile Cys Asn
            195             200             205

Val Asn His Lys Pro Ser Asn Thr Lys Val Asp Lys Lys Val Glu Pro
    210             215             220

Lys Ser Cys Asp Lys Thr His Thr Cys Pro Pro Cys Pro Ala Pro Glu
225             230             235             240

Leu Leu Gly Gly Pro Ser Val Phe Leu Phe Pro Pro Lys Pro Lys Asp
            245             250             255

Thr Leu Met Ile Ser Arg Thr Pro Glu Val Thr Cys Val Val Val Asp
            260             265             270

Val Ser His Glu Asp Pro Glu Val Lys Phe Asn Trp Tyr Val Asp Gly
            275             280             285

Val Glu Val His Asn Ala Lys Thr Lys Pro Arg Glu Glu Gln Tyr Asn
    290             295             300

Ser Thr Tyr Arg Val Val Ser Val Leu Thr Val Leu His Gln Asp Trp
305             310             315             320

Leu Asn Gly Lys Glu Tyr Lys Cys Lys Val Ser Asn Lys Ala Leu Pro
            325             330             335

Ala Pro Ile Glu Lys Thr Ile Ser Lys Ala Lys Gly Gln Pro Arg Glu
            340             345             350

Pro Gln Val Tyr Thr Leu Pro Pro Ser Arg Asp Glu Leu Thr Lys Asn
            355             360             365

Gln Val Ser Leu Thr Cys Leu Val Lys Gly Phe Tyr Pro Ser Asp Ile
    370             375             380

Ala Val Glu Trp Glu Ser Asn Gly Gln Pro Glu Asn Asn Tyr Lys Thr
385             390             395             400

Thr Pro Pro Val Leu Asp Ser Asp Gly Ser Phe Phe Leu Tyr Ser Lys
            405             410             415

Leu Thr Val Asp Lys Ser Arg Trp Gln Gln Gly Asn Val Phe Ser Cys
            420             425             430

Ser Val Met His Glu Ala Leu His Asn His Tyr Thr Gln Lys Ser Leu
            435             440             445

Ser Leu Ser Pro Gly Lys
    450
```

<210> SEQ ID NO 71
<211> LENGTH: 214
<212> TYPE: PRT
<213> ORGANISM: Artificial Sequence
<220> FEATURE:
<223> OTHER INFORMATION: CTLA4-8 LC amino acid sequence - Artificial
      sequence translated from an isolated clone of an RNA display
      library -continued

```
<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

ANTI-CTLA4 MONOCLONAL ANTIBODIES AND CHIMERIC ANTIGEN RECEPTORS

This application is a 371 application of PCT/IB2021/055076, which was filed Jun. 9, 2021 and which claims priority to US Provisional Patent Application with the Ser. No. 63/038,111, which was filed Jun. 11, 2020, and which is incorporated by reference in its entirety.

SEQUENCE LISTING

The content of the ASCII text file of the sequence listing with the file name 102719.0032US_Seq_listing.txt, which is 112,204 bytes in size and was created on 06/01/2021 and which was electronically submitted via EFS-Web. The aforementioned sequence listing is incorporated by reference in its entirety.

FIELD OF THE INVENTION

The field of the invention is compositions and methods for compounds that bind to cytotoxic T lymphocyte-associated antigen-4 (CTLA-4), and especially antibodies, antibody fragments, scFvs, and fusion molecules comprising VH and VL domains as presented herein.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Immunotherapy has increasingly become a promising therapeutic strategy against various cancers. Among other options, cancer vaccine compositions, typically in combination with immune stimulatory drugs, have shown in at least some approaches significant therapeutic effect. Unfortunately, the tumor microenvironment often has an immune suppressive effect of T cells and NK cells and immune therapies are often rendered less effective. Cytotoxic T lymphocyte-associated antigen-4 (CTLA-4, CD152) is a membrane glycoprotein expressed by activated effector T cells (Teff) and participates in the repression of T cell proliferation, cell cycle progression and cytokine (IL-2, IFN-γ) production. CTLA-4 is thought to exert its inhibitory function through multiple mechanisms including competition with CD28-positive co-stimulation for binding to their shared B7 ligands (CD80/CD86) on the antigen-presenting cells (APC), as well as direct inhibitory effects through the cytoplasmic tail which associates with signaling molecules.

To overcome immune suppression due to CTLA-4 activity, anti-CTLA-4 antibodies can be used as a therapeutic effector. Currently known anti-CTLA-4 antibodies include ipilimumab and tremelimumab, which have been used, alone or in combination with chemotherapy, cancer vaccines, or other antibodies (anti-PD-1 or anti-OX40), in the treatment of various cancers, including melanoma, non-small cell lung cancer (NSCLC), breast cancer, prostate cancer, pancreatic cancer, hepatocellular carcinoma, and mesothelioma. Ipilimumab produced increased long-term survival at a dose of 10 mg/kg in melanoma and had anti-tumor activity in patients with B-cell lymphoma. However, ipilimumab was not shown effective in patients with metastatic castration-resistant prostate cancer. Although it did not show similar benefit as ipilimumab, clinical trials for tremelimumab demonstrated acceptable tolerability and clinically meaningful activity in patients with melanoma, refractory metastatic colorectal cancer, hepatocellular carcinoma and malignant mesothelioma.

Unfortunately, ipilimumab and tremelimumab have significant adverse effects and are not always effective in reducing immune suppression. Thus, even though various systems and methods of interfering with CTRLA-4 signaling are known in the art, all or almost all of them suffer from several drawbacks. Therefore, there remains a need for compositions and methods for improved compounds that bind to CTLA-4.

SUMMARY OF THE INVENTION

The inventive subject matter is directed to various compositions and methods of polypeptides that bind with high specificity and affinity to CTLA-4. In preferred embodiments, the polypeptides are configured as scFvs, antibodies, or portions thereof, or as chimeric molecules such as CARs, N-803 or TxM derivatives. In further preferred embodiments, the polypeptides comprise a VH and/or VL domain and have an amino acid sequence as described in SEQ ID NO. 1-59, or comprise a heavy or a light chain of an antibody as described in SEQ ID NO:60-71. As will be readily appreciated, these polypeptides can be employed in various diagnostic and therapeutic uses, and especially in the reduction of immune suppression and treatment of cancer.

In one aspect of the inventive subject matter, the inventors contemplate a single chain variable fragment (scFv) peptide that includes a $V_H$ segment comprising a first amino acid sequence selected from the group consisting of SEQ ID NO. 1, 3, 5, 7, 9, 11, 13, 15, 17, 19, 21, 23, 25, 27, 29, 31, 33, 35, 36, 38, 40, 42, 44, 46, 48, 49, 51, 54, 56, and 58, and/or a $V_L$ segment comprising a second amino acid sequence selected from the group consisting of SEQ ID NO. 2, 4, 6, 8, 10, 12, 14, 16, 18, 20, 22, 24, 26, 28, 30, 32, 34, 37, 39, 41, 43, 45, 47. 50, 53, 55, 57, and 59. Most typically, the $V_H$ segment and $V_L$ segment are coupled with a linker peptide (e.g., a glycine-rich peptide). Moreover, it is contemplated that the single chain variable fragment (scFv) peptide may further comprise at least two pairs of the $V_H$ segment and $V_L$ segment, wherein the at least two pairs are linked to form a multivalent scFv. Where desired the peptide may be present in the pharmacologically acceptable carrier.

In another aspect of the inventive subject matter, the inventors contemplate an antibody that comprises a heavy chain comprising a first amino acid sequence selected from the group consisting of SEQ ID NO. 60, 61, 62, 64, 65, 66, 68, and 70, and/or a light chain comprising a second amino acid sequence selected from the group consisting of SEQ ID NO. 63, 67, 69, and 71. For example, suitable antibodies include those having a heavy chain comprising a first amino acid sequence of SEQ ID NO. 68 and a light chain comprising a second amino acid sequence of SEQ ID NO. 69, or a heavy chain comprising a first amino acid sequence of SEQ ID NO. 70 and a light chain comprising a second amino acid sequence of SEQ ID NO. 71.

In a further aspect of the inventive subject matter, the inventors contemplate a pharmaceutical composition for treating a patient having a cancer that includes a single chain variable fragment (scFv) peptide or an antibody as presented herein, wherein the single chain variable fragment (scFv) peptide or the antibody is present in a pharmacologically acceptable carrier.

In still another aspect of the inventive subject matter, the inventors contemplate a diagnostic composition that comprises a single chain variable fragment (scFv) peptide or an antibody as presented herein wherein the single chain variable fragment (scFv) peptide or the antibody further comprises a detectable label.

Moreover, the inventors also contemplate a recombinant nucleic acid, comprising: first nucleic acid segment encoding a first amino acid sequence selected from the group consisting of SEQ ID NO. 1, 3, 5, 7, 9, 11, 13, 15, 17, 19, 21, 23, 25, 27, 29, 31, 33, 35, 36, 38, 40, 42, 44, 46, 48, 49, 51, 54, 56, and 58, and/or a second amino acid sequence selected from the group consisting of SEQ ID NO. 2, 4, 6, 8, 10, 12, 14, 16, 18, 20, 22, 24, 26, 28, 30, 32, 34, 37, 39, 41, 43, 45, 47. 50, 53, 55, 57, and 59. Preferably, but not necessarily, the first and second segments are present in a same reading frame. Additionally, the inventors contemplate a recombinant nucleic acid that comprises a first nucleic acid segment encoding a first amino acid sequence selected from the group consisting of SEQ ID NO. 60, 61, 62, 64, 65, 66, 68, and 70, and/or a second amino acid sequence selected from the group consisting of SEQ ID NO. 63, 67, 69, and 71. Preferably, but not necessarily, the first and second segments are in a bicistronic arrangement.

For example, contemplated recombinant nucleic acids may comprise a first nucleic acid segment encoding a first amino acid sequence of SEQ ID NO. 68 and second nucleic acid segment encoding a second amino acid sequence of SEQ ID NO. 69, or a first nucleic acid segment encoding a first amino acid sequence of SEQ ID NO. 70 and a second nucleic acid segment encoding a second amino acid sequence of SEQ ID NO. 71.

As will be readily appreciated, the recombinant nucleic acid may further comprise a third segment encoding a polypeptide that encodes at least a portion of a chimeric antigen receptor (CAR), wherein the CAR, when expressed in the cell, has an antigen binding ectodomain that comprises the first and/or second nucleic acid segment. Alternatively, the recombinant nucleic acid may also comprises a third segment encoding a polypeptide that encodes at least a portion of a N-803 or TxM, wherein the N-803 or TxM, when expressed in the cell, has an antigen binding domain that comprises the first and/or second nucleic acid segment.

Therefore, the inventors also contemplate a recombinant cell that includes (e.g., via transfection or genetic engineering) a recombinant nucleic acid as described above. Among other suitable cell types, the recombinant cell may be a recombinant T cell, a recombinant NK cell, a recombinant NKT cell, a recombinant monocyte, a recombinant macrophage, or a recombinant dendritic cell. Alternatively, the recombinant cell may also be a production cell engineered to produce a recombinant protein such as a CHO cell or EC7 cell.

In still further contemplated aspects, a method of reducing an CTLA-4-mediated effect in a cell or tissue is presented that includes a step of contacting the cell or tissue with a single chain variable fragment (scFv) peptide an antibody as presented herein in an amount that reduces the CTALA-4-mediated effect in the cell or tissue.

Consequently, the inventors also contemplate a method of treating a patient having a tumor that includes a step of administering to the patient a pharmaceutical composition that comprises a single chain variable fragment (scFv) peptide or an antibody as presented herein, or a recombinant cell as presented herein. Most preferably, the pharmaceutical composition is administered to the patient in a dose and a schedule effective to treat the tumor.

Therefore, and viewed from a different perspective, the inventors also contemplate a method of reducing immune suppression in a patient having a tumor that includes a step of administering to the patient a pharmaceutical composition that comprises a single chain variable fragment (scFv) peptide or an antibody as presented herein, or a recombinant cell as presented herein. Most preferably, the pharmaceutical composition is administered to the patient in a dose and a schedule effective to reduce immune suppression in a tumor microenvironment.

Thus, use of a single chain variable fragment (scFv) or antibody or recombinant cell as presented herein is contemplated for use in medicine, and especially for treating a cancer and/or reducing immune suppression in a patient having a tumor.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
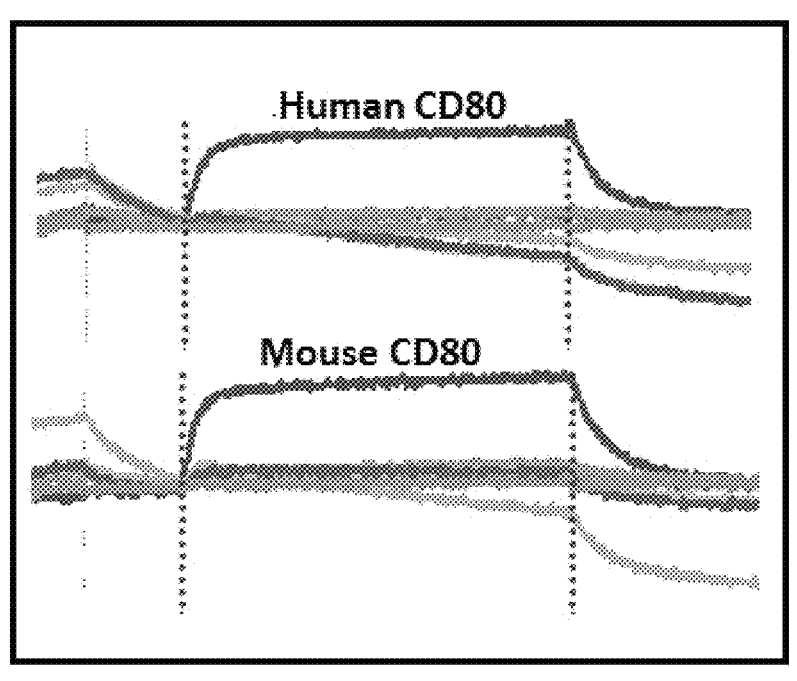
FIG. 1 depicts exemplary SPR results for various scFv constructs as presented herein.

The inventors have discovered various polypeptides that have significant binding to CTLA-4, and particularly VH and VL domains of antibodies or fragments or fusion proteins containing the VH and/or VL domains (and CDRs contained therein). Most advantageously, the VH and/or VL domains or CDRs contained therein can be used to generate various therapeutic or diagnostic agents with high affinity and specificity towards CTLA-4.

With respect to the VH and VL domains contemplated herein it should be appreciated that the domains generally follow well-known nomenclature. As such, the VH domain denotes the variable fragment of a heavy chain in an antibody that is typically bound to several constant domains (e.g., VH domain bound to CH1, CH2, and CH3 domains in an IgG). Likewise, the VL domain denotes that variable fragment of a light chain in an antibody that is typically bound to a constant domain (e.g., VL domain bound to CL in an IgG). As will therefore be readily appreciated, each of the VH and VL domains will have respective framework regions (FR) and complementarity determining regions (CDR), typically sequentially arranged as FR1-CDR1-FR2-CDR2-FR3CDR3-FR4. Consequently, based on the known framework regions in a VH and VL domain, the skilled artisan will readily recognize the respective CDRs in the VH or VL domain. The terms "domain" and "segment" in their conjunction with VH or VL are used interchangeably herein.

As will be further readily recognized, the skilled artisan will be able to use the amino sequences of VH segments and/or VL segments to generate a recombinant, isolated antibody or fragment thereof. As used herein, the term "antibody" refers to immunoglobulin molecules and immunologically active portions of immunoglobulin molecules, i.e., molecules that contain an antigen-binding site that immune-specifically bind an antigen. Thus, "antibody and the fragment thereof" includes a whole immunoglobulin molecule (e.g., a full-size, whole IgG$_1$, IgA, etc.), and an antigen-binding fragment of the whole immunoglobulin molecule. Thus, contemplated fragments include an scFv, Fab fragments, Fab' fragments, F(ab')2, disulfide linked Fvs (sdFvs), Fvs, and any fragment comprising either V$_H$ segment and/or V$_L$ segment. Where the antibody is an immunoglobulin, it is contemplated that the immunoglobulin can include any type (e.g., IgG, IgE, IgM, IgD, IgA, or IgY) and any class (e.g., IgG$_1$, IgG$_2$, IgG$_3$, IgG$_4$, IgA$_1$ or IgA$_2$) of heavy chain or constant domain to constitute different types of immunoglobulins. In addition, the "antibody" will especially include a human antibody, a humanized antibody, a chimeric antibody, a monoclonal antibody, and a polyclonal antibody. Thus, it should be appreciated that the VH and/or VL domains of SEQ ID NOs. 1-59 can be grafted into any existing (typically human or humanized) antibody or antibody fragment using methods well known in the art.

The inventors further contemplated that the that the amino sequences of VH segments and/or VL segments presented in SEQ ID NOs. 1-59 can be used coupled with a carrier protein to generate a hybrid protein having the VH segments and/or VL segments on its surface such that CTLA-4 can be bound or blocked by the hybrid protein. Any suitable form of carrier protein that can stably carry a VH segment and/or a VL segment and preferably provide an access to a tumor microenvironment is contemplated. One especially preferred carrier protein includes albumin, refolded albumin, and other proteins with affinity to antibody portions (e.g., protein A, protein G, protein Z) coupled with one or more VH segments and/or VL segments.

Typically, VH segments and/or VL segments are coupled with an anchor molecule by which VH segments and/or VL segments can be coupled with the carrier protein. For example, where the carrier protein is an albumin, the anchor molecule can be a hydrophobic peptide or glycolipids in any suitable size to fit in one of Sudlow site I and II of the albumin or any other hydrophobic area of the albumin. For example, the recombinant immunoglobulin protein against CTLA-4 as described above can be coupled with the carrier protein via its Fc domain. In other embodiments, the anchor molecule may include a hydrophobic peptide (in a length of at least 10 amino acids, 15 amino acids, 20 amino acids, 30 amino acids, etc.). In these embodiments, various configurations of VH segments and/or VL segments (e.g., as a form of scFv) and hydrophobic peptides can be contemplated. For example, a monovalent scFv domain can be directly linked to a hydrophobic peptide, or a multivalent scFv can be directly linked to a hydrophobic peptide. Alternatively, one scFv domain can be directly linked to a plurality of hydrophobic peptides or a plurality of scFv domain can be directly linked to a plurality of hydrophobic peptides.

Alternatively, or additionally, one or more VH segments and/or VL segments can be coupled with an intermediate molecule that has an anchor portion to bind to the carrier protein. In a preferred embodiment, the inventors contemplate that the intermediate molecule provides a plurality of binding sites for VH segments and/or VL segments such that multiple target recognition domains can be carried via a single binding site on the carrier protein. Suitable intermediate molecule may include any protein, glycolipid, organic molecule, or inorganic molecule that does not provide any significant toxicity to the naïve tissue. For example, the suitable intermediate molecule may include a nanoparticle (e.g., quantum dots, gold nanoparticles, magnetic nanoparticles, nanotubes, polymeric nanoparticles, dendrimers, etc.), or a bead (e.g., polystyrene bead, latex bead, dynabead, etc.). Preferably, the nanoparticle and/or beads have a dimension below 1 μm, preferably below 100 nm. The nanoparticle may be crosslinked to or partially coated with a hydrophobic tail that provide an anchor to the carrier protein (e.g., albumin). One or more VH segments and/or VL segments can be also crosslinked to or partially coated on the nanoparticles (e.g., via an extra tail domain linked to the target recognition domain for crosslinking, etc.).

In another example, suitable intermediate molecules may include beads (e.g., polystyrene beads, latex beads, dynabeads, etc.) coupled with an antibody against the carrier protein. Thus, where the carrier protein is an albumin, the beads can be coupled (e.g., crosslinked, coated, etc.) with α-albumin antibody such that the bead can bind to the carrier protein with a high affinity and specificity. One or more VH segments and/or VL segments can be also crosslinked to or partially coated on the bead (e.g., via an extra tail domain linked to the target recognition domain for crosslinking, thiol-mediated crosslinking, etc.).

In some embodiments, scFv peptide can form a recombinant immunoglobulin protein complex that comprises or mimics an ALT-803 (IL-15 superagonist complex, see e.g., *Blood* 2015 126:1957) or TxM (targeted ALT-803-based scaffold platform, see e.g., URL altorbioscience.com/our-science/il-15-protein-superagonist-and-scaffold-technology/) structure. Preferably, the inventors contemplate that, where the immunoglobulin protein complex mimics TxM structure, the scFv peptide can be directly (or indirectly via a linker) coupled to one or more interleukin-15 (IL-15) binding motif, and/or one or more ligand to the IL-15 binding motif (e.g., IL-15, IL-15N72D, etc.). Thus, where the recombinant immunoglobulin protein complex mimics TxM IgG$_1$ structure, the recombinant immunoglobulin protein complex may include 1-4 scFv peptide against CTLA-4.

Additionally, the recombinant immunoglobulin protein complex mimicking the TxM structure having one or more scFv peptides coupled with IL-15 binding motif or its ligand may also include a binding domain against a tumor specific antigen or patient- and tumor specific neoepitope (e.g., an scFv peptide against a neoepitope, etc). For example, the recombinant immunoglobulin protein complex may include two scFv peptides against CTLA-4 coupled with two IL-15 binding motives and two ScFv peptides against the neoepitope coupled with two IL-15 binding motif ligands. Preferably, the neoepitope is patient-specific and tumor-specific, which is identified by omics analysis of the sequence data as disclosed, for example, in US 2012/0059670A1 and US 2012/0066001A1.

In some embodiments, the scFv, recombinant antibody or fragment thereof, can be generated using one sequence encoding a VH segment among SEQ ID NO. 1, 3, 5, 7, 9, 11, 13, 15, 17, 19, 21, 23, 25, 27, 29, 31, 33, 35, 36, 38, 40, 42, 44, 46, 48, 49, 51, 54, 56, and 58. In other embodiments, the scFv, recombinant antibody or fragment thereof, can be generated using one sequence encoding a VL segment among SEQ ID NO. 2, 4, 6, 8, 10, 12, 14, 16, 18, 20, 22, 24, 26, 28, 30, 32, 34, 37, 39, 41, 43, 45, 47. 50, 53, 55, 57, and 59. In still other embodiments, the scFv, recombinant antibody or fragment thereof, can be generated using one sequence encoding a VH segment among SEQ ID NO. 1, 3, 5, 7, 9, 11, 13, 15, 17, 19, 21, 23, 25, 27, 29, 31, 33, 35, 36, 38, 40, 42, 44, 46, 48, 49, 51, 54, 56, and 58 and one sequence encoding a VL segment among SEQ ID NO. 2, 4, 6, 8, 10, 12, 14, 16, 18, 20, 22, 24, 26, 28, 30, 32, 34, 37, 39, 41, 43, 45, 47. 50, 53, 55, 57, and 59. In these embodiments, it is preferred that the sequence encoding the VH segment and sequence encoding the VL segment are paired having a common designator in the sequence listing with a distinguishing VH and VL identifier (e.g., 73-2 VH and 73-2 VL, as shown in SEQ ID NO. 1 and 2, respectively). However, as is shown in more detail below, it is also contemplated that any pair of VH segment and VL segment can be generated to form a CTLA-4 binding molecule by selecting one VH segment from SEQ ID No. xx and one VL segment from SEQ ID No. yy, with xx being any one of 1, 3, 5, 7, 9, 11, 13, 15, 17, 19, 21, 23, 25, 27, 29, 31, 33, 35, 36, 38, 40, 42, 44, 46, 48, 49, 51, 54, 56, and 58, and with yy being any one of 2, 4, 6, 8, 10, 12, 14, 16, 18, 20, 22, 24, 26, 28, 30, 32, 34, 37, 39, 41, 43, 45, 47. 50, 53, 55, 57, and 59.

The inventors also contemplate that the scFv, recombinant antibody or fragment thereof, can be generated with amino acid sequences encoding VH segment and/or VL segment that are at least 85% identical, preferably at least 90% identical, more preferably at least 95% identical to any one of SEQ ID No. xx or yy. Most typically, where the identity is not 100%, the differing amino acid(s) will be located in one or more of the framework regions of the sequences and will not affect the CDR regions of a given sequence. In further embodiments, it is preferred that the binding affinity of the scFv peptide, recombinant antibody or fragment thereof, is no higher than 100 nM, or no higher than 50 nM, or no higher than 20 nM, or no higher than 10 nM, or no higher than 5 nM, or no higher than 2 nM, or no higher than 1 nM. For example, one could select any scFv with a specific VH and/or VL domain as presented herein and then subjected the scFv to affinity maturation via random mutagenesis in the CDR regions for VH and VL. In such examples, it is typically contemplated that no more than 4, or nor more than 3, or no more than 2 amino acids will be changed across all CDR regions of a given sequence. As will be recognized, multiple binders can therefore be isolated from the affinity maturation process with improved binding characteristics.

Most typically, the VH segment and VL segment in an scFv peptide or similar construct are coupled via a linker or a spacer, which is typically between 5-40 amino acids, preferably between $10^{-30}$ amino acids, more preferably between 20-30 amino acids. In some embodiments, the linker can couple the N-terminus of VH segment and C-terminus of VL segment. In other embodiments, the linker can couple the N-terminus of VL segment and C-terminus of VH segment. The inventors further contemplate that glycine-rich sequences (e.g., $(G_4S)n$, with n between 1-5, etc.) for the linker are preferred to provide structural flexibility between the VH segment and VL segments. It is also contemplated that the linker includes one or more serine or threonine residue to increase solubility of the scFv peptide, recombinant antibody or fragment thereof. There are numerous linkers and methods of making scFv known in the art, and all such known methods are deemed suitable for use herein.

Additionally, the scFv peptide can include a plurality of VH segments and VL segments to form a divalent or multivalent scFv. In some embodiments, the plurality of VH segments and/or VL segments may have same amino sequences (e.g., a multivalent scFv having three VH segments and three VL segments, and all VH segments have the same VH and all VL segments have the same VL domain. In other embodiments, at least two of VH segments and/or VL segments may have different amino acid sequences (e.g., a multivalent scFv having three VH segments and three VL segments, and two of VH segments are identical VH domains and one of VH segments is distinct, and two of VL segments are identical VL domains and one of VH segments is distinct.

Preferably, the binding affinity (Kd) of the scFv, recombinant antibody or fragment thereof, to CTLA-4 (at least one of 72-mer and 77-mer IL-8) is at least less than $1\times10^{-7}$M, preferably less than $1\times10^{-8}$M, and more preferably less than $1\times10^{-9}$M, measured at a temperature between 25° C. to 37° C., and measured in a pH range between 5.5-7.5. The inventors contemplate that the binding affinities of the scFv, recombinant antibody or fragment thereof, to CTLA-4 may be different due to the structural differences even if the scFv, recombinant antibody or fragment thereof, are generated using the same amino acid sequences of $V_H$ segment and/or $V_L$ segments. For example, Tables 1~4 provide different affinities (measured in KD value) of different scFv clones, while Table 5 shows different affinities (measured in KD value) of different recombinant antibody (IgG1) clones.

It is further contemplated that the scFv peptide (or VH segment and VL segment of an antibody or fragment thereof) can be encoded by a single recombinant nucleic acid. In such embodiment, the recombinant nucleic acid includes at least two nucleic acid segments: a first nucleic acid segment encoding the VH segment and a second nucleic acid segment encoding the VL segment of the inventive subject matter. However, it is also contemplated that the first and second nucleic acid segments that the encode VH and VL segment respectively that are at least 85% identical, preferably at least 90% identical, more preferably at least 95% identical to any one of SEQ ID No. 1-59. Most preferably, the two nucleic acid segments are in the same reading frame such that two nucleic acid segments can be translated into a single protein having two peptide segments.

Additionally, the recombinant nucleic acid may include a third nucleic acid segment between the first and second nucleic acid segment encoding a linker peptide (preferably G-rich or otherwise flexible linker peptide), which is typically between 5-40 amino acids, preferably between 10-30 amino acids, more preferably between 20-30 amino acids. In this embodiment, it is especially preferred that the three nucleic acid segments are in the same reading frame such that three nucleic acid segments can be translated into a single protein having three peptide segments.

On the other hand, where the CTLA-4 binding molecule is an antibody (e.g., IgG), the VH segment and VL segment as presented herein may be encoded on single recombinant bicistronic construct or the segments may be encoded on two separate constructs. Most typically, the nucleic acid encoding the VH domain will also encode in frame one or more CH domains (e.g., CH1-CH2-CH3 in case of an IgG). Likewise, the nucleic acid encoding the VL domain will also encode in frame one CH domain (e.g., CL in case of an IgG). Most typically, the constant domains for heavy and light chains will be human humanized, but other mammalian sequences are also deemed appropriate. Moreover, it should be recognized that the recombinant nucleic acids will preferably (but not necessarily) have a codon usage that is optimized for the cell expressing the antibody.

The inventors further contemplate that the scFv peptide, antibodies or fragments thereof, can be formulated as a pharmaceutical composition so that it can be administered to the patient having a tumor to reduce or inhibit signaling and attendant immune suppression by CTLA-4. Therefore, it is contemplated that the scFv peptide, antibodies or fragments thereof, can be formulated in any pharmaceutically acceptable carrier (e.g., as a sterile injectable composition) in an amount of at least 1 ml, preferably at least 5 ml, more preferably and at least 20 ml per dosage unit for a therapeutic formulation. However, alternative formulations are also deemed suitable for use herein, and all known routes and modes of administration are contemplated herein. As used herein, the term "administering" refers to both direct and indirect administration of the compounds and compositions contemplated herein, where direct administration is typically performed by a health care professional (e.g., physician, nurse, etc.), while indirect administration typically includes a step of providing or making the compounds and compositions available to the health care professional for direct administration. In some embodiments, the pharmaceutical formulation is administered via systemic injection including subcutaneous, subdermal injection, or intravenous injection. In other embodiments, and as shown in more detail below, it is contemplated that the formulation is administered via intratumoral injection.

One exemplary method and use of pharmaceutical composition including scFv peptide, the antibody or fragment thereof, which includes VH and VL segments described above is to reduce CTLA-4 mediated effects in a target tissue or target cell. As used herein, the CTLA-4 mediated effect refers to any biological consequence induced directly or indirectly by activity of CTLA-4 in the tissue or the microenvironment of the tissue. Most typically, the effect is observable as a reduction in T cell activity (and especially cytotoxic cell killing by T cells and NK cells), which may be enhanced or observed in a tumor microenvironment. Viewed from a different perspective, the reduction of IL-8 mediated effects in vivo can also be observed by physiological phenomena. For example, reduced CTLA-4 signaling can be observed via reduction or abolishment of tumor growth, by tumor shrinkage, tumor cell apoptosis or necrosis. Similarly, reduced CTLA-4 signaling in a patient and especially in a tumor microenvironment will reduce the tendency of a tumor to produce local or distant metastases.

With respect to dose and schedule of the pharmaceutical composition administration to a patient, it is contemplated that the dose and/or schedule may vary depending on the type of peptides (e.g., scFv, an antibody, an antibody fragment, combination of any two of those, combination of all, etc.), type and prognosis of disease (e.g., tumor type, size, location), health status of the patient (e.g., including age, gender, etc.). While it may vary, the dose and schedule may be selected and regulated so that the formulation does not provide any significant toxic effect to the host normal cells, yet sufficient to be reduce CTLA-4 effect in the tumor microenvironment at least 20%, preferably at least 30%, more preferably at least 40%, most preferably at least 50% within less than 3 hours, 6 hours, 12 hours, 24 hours, 72 hours, or a week. For example, where the CTLA-4 binder is an antibody, suitable doses of the antibody may be between 0.1-1.0 mg, or between 1.0-5.0 mg, or between 5.0-10.0 mg, or between 10-50 mg, or between 50-100 mg per administration.

Additionally, the inventors contemplate that the effect of scFv, antibody or fragment thereof against CTLA-4 can be boosted by co-administration of one or more cancer medications. The cancer medications includes, but not limited to, Fulvestrant, Aldoxorubicin, Docetaxel, a tumor necrosis treatment agent (e.g., [131] I-chTNT-3, etc.), Avelumab (a human monoclonal $IgG_1$ antibody that blocks interaction between PD-L1 and its receptor), Brachyury-targeting vaccine (e.g., ETBX-051 (Ad5 [E1-, E2b-]-Brachyury)), Her2-targeting vaccine (e.g., ETBX-021, etc.), MUC-1-targeting vaccine (e.g., ETBX-061 (Ad5 [E1-, E2b-]-MUC1)), and yeast vaccines (e.g., GI-4000 (GI-4014, GI-4015, GI-4016, GI-4020), GI-6207, GI-6301), and adenovirus or yeast based vaccines against tumor specific neoepitopes. Exemplary details of these cancer medications are described in PCT/US17/40297, which is incorporated herein as a reference in its entirety.

Where desired, the CTLA-4 binding agent may also be co-administered with a cell-based treatment (at the same time or separated by one or more days), and especially preferred cell-based treatments include transfusion with NK cells and/or T cells. Of course, it should be appreciated that such cells may be genetically modified to express one or more recombinant molecules to so increase target specific tumor cell killing.

In especially preferred aspects, such modified NK cells or T cells may be engineered to express a chimeric antigen receptor (CAR). In some embodiments, the CAR of the NK cells or T cells may target one or more cancer- or tumor specific antigens, while in especially contemplated embodiments the CAR expressed by the NK cells or T cells will target CTLA-4. In general, it is noted that suitable CARs comprise a single-chain variable fragment (scFv) linked to at least one intracellular signaling domain. The scFv recognizes and binds an antigen on the target cell (e.g., antigen or CTLA-4) and triggers effector cell activation. The signaling domains contain in most cases immunoreceptor tyrosine-based activation domains (ITAMs) that are important for intracellular signaling by the receptor. Suitable CARs include first, second, and third generation CARs that can be expressed in a variety of cells, and especially T cells and NK cells.

First generation CARs will typically contain one cytoplasmic signaling domain. For example, one version of a first-generation CAR in T-cells may include a signaling domain from the Fc epsilon receptor gamma (FcεRIγ) that contains one ITAM, while another version may contain the signaling domain from CD3ζ which contains three ITAMs. Second generation CARs typically employ CD28 as the most common intracellular costimulatory domain alongside CD3ζ. Alternatively, second generation CARs may also incorporate the 4-1BB intracellular signaling domain along with CD3ζ. Third generation CARs will typically include CD3ζ, CD28, and 4-1BB intracellular signaling domains. See also WO 2016/201304 and WO 2018/076391 for further third generation CARs.

EXAMPLES

Affinity of selected scFv molecules to human CTLA-4 was performed via surface plasmon resonance (SPR). More specifically, a Pioneer FE instrument was used to measure the binding affinities between scFv and the recombinant CTLA-4 protein at 25° C. Briefly, biotinylated anti-FLAG M2 antibody was immobilized onto the PCH biosensor (Molecular Devices/ForteBio) coated with neutravidin. 3×FLAG-tagged scFvs were captured with anti-FLAG M2 on the sensor and the binding affinities were measured using OneStep injection with recombinant human CTLA-4 protein. Exemplary results for selected scFvs are shown in Tables 1 and 2 below. In the clone designations of the tables 1-4 below, it should be noted that the clone for the scFv includes both, the VH and VL domain with the SEQ ID NOs as indicated.

TABLE 1

| Affinity for scFvs to human CTLA-4 | |
| --- | --- |
| Clone | $K_D$ (nM) |
| 73-2 (SEQ ID NO: 1, SEQ ID NO: 2) | 0.56 |
| 74-1 (SEQ ID NO: 3, SEQ ID NO: 4 | 1.92 |
| 78-8 (SEQ ID NO: 11, SEQ ID NO: 12) | 168 |
| 78-8D2 (SEQ ID NO: 13, SEQ ID NO: 14 | 0.37 |
| 78-8D4 (SEQ ID NO: 15, SEQ ID NO: 16) | 0.21 |
| 78-8D5 (SEQ ID NO: 17, SEQ ID NO: 18) | 0.74 |
| 78-8D6 (SEQ ID NO: 19, SEQ ID NO: 20) | 0.24 |
| 78-8D7 (SEQ ID NO: 21, SEQ ID NO: 22) | 0.30 |
| 78-8D10 (SEQ ID NO: 23, SEQ ID NO: 24 | 0.58 |
| 78-8D14 (SEQ ID NO: 25, SEQ ID NO: 26) | 0.32 |
| 78-8D22 (SEQ ID NO: 27, SEQ ID NO: 28 | 0.16 |

TABLE 2

| Affinity for scFvs to human CTLA-4 | |
| --- | --- |
| Clone | $K_D$ (nM) |
| 78-24 (SEQ ID NO: 33, SEQ ID NO: 34) | 136 |
| 78-24D1 (SEQ ID NO: 35, SEQ ID NO: 36) | 1.15 |
| 78-24D4 (SEQ ID NO: 38, SEQ ID NO: 39) | 1.17 |
| 78-24D8 (SEQ ID NO: 40, SEQ ID NO: 41) | 1.46 |
| 78-24D9 (SEQ ID NO: 42, SEQ ID NO: 43) | 1.18 |
| 78-24D12 (SEQ ID NO: 44, SEQ ID NO: 45) | 2.88 |
| 78-24D14 (SEQ ID NO: 46, SEQ ID NO: 47) | 4.6 |
| 78-24D17 (SEQ ID NO: 48, SEQ ID NO: 50) | 0.87 |
| 78-24D22 (SEQ ID NO: 51, SEQ ID NO: 53) | 0.85 |

Similarly, affinity of selected scFv molecules to murine CTLA-4 was performed via surface plasmon resonance (SPR). More specifically, a Pioneer FE instrument was used to measure the binding affinities between scFv and the recombinant CTLA-4 protein at 25° C. Briefly, biotinylated anti-FLAG M2 antibody was immobilized onto the PCH biosensor (Molecular Devices/ForteBio) coated with neutravidin. 3×FLAG-tagged scFvs were captured with anti-FLAG M2 on the sensor and the binding affinities were measured using OneStep injection with recombinant mouse CTLA-4 protein. Exemplary results for selected scFvs are shown in Tables 3 and 4 below.

TABLE 3

| Affinity for scFvs to mouse CTLA-4 | |
| --- | --- |
| Clone | scFv KD (nM) |
| 78-1 (SEQ ID NO: 5, SEQ ID NO: 6) | 0.61 |
| 78-2 (SEQ ID NO: 7, SEQ ID NO: 8) | 0.55 |
| 78-5 (SEQ ID NO: 9, SEQ ID NO: 10) | 0.64 |
| 78-8 (SEQ ID NO: 11, SEQ ID NO: 12) | 0.06 |
| 78-8D2 (SEQ ID NO: 13, SEQ ID NO: 14) | 0.30 |
| 78-8D4 (SEQ ID NO: 15, SEQ ID NO: 16) | 0.20 |
| 78-8D5 (SEQ ID NO: 17, SEQ ID NO: 18) | 0.42 |
| 78-8D6 (SEQ ID NO: 19, SEQ ID NO: 20) | 0.19 |
| 78-8D7 (SEQ ID NO: 21, SEQ ID NO: 22) | 0.39 |
| 78-8D10 (SEQ ID NO: 23, SEQ ID NO: 24) | 0.49 |
| 78-8D14 (SEQ ID NO: 25, SEQ ID NO: 26) | 0.17 |
| 78-8D22 (SEQ ID NO: 27, SEQ ID NO: 28) | 0.37 |
| 78-13 (SEQ ID NO: 29, SEQ ID NO: 30) | 0.79 |

TABLE 4

| Affinity for scFvs to mouse CTLA-4 | |
| --- | --- |
| Clone | scFv $K_D$ (nM) |
| 78-19 (SEQ ID NO: 31, SEQ ID NO: 32) | 2.39 |
| 78-24 (SEQ ID NO: 33, SEQ ID NO: 34) | 2.17 |
| 78-24D1 (SEQ ID NO: 35, SEQ ID NO: 37) | 0.059 |
| 78-24D4 (SEQ ID NO: 38, SEQ ID NO: 39) | 1.03 |
| 78-24D8 (SEQ ID NO: 40, SEQ ID NO: 41) | 0.01 |
| 78-24D9 (SEQ ID NO: 42, SEQ ID NO: 43) | 1.11 |
| 78-24D12 (SEQ ID NO: 44, SEQ ID NO: 45) | 0.01 |
| 78-24D14 (SEQ ID NO: 46, SEQ ID NO: 47) | 0.19 |
| 78-24D17(SEQ ID NO: 48, SEQ ID NO: 50) | 1.06 |
| 78-24D22 (SEQ ID NO: 51, SEQ ID NO: 53) | 0.05 |
| 78-28 (SEQ ID NO: 54, SEQ ID NO: 55) | 2.57 |
| 78-36 (SEQ ID NO: 56, SEQ ID NO: 57) | 0.98 |
| 78-39 (SEQ ID NO: 58, SEQ ID NO: 59) | 0.97 |

In still further experiments, selected VH and VL domains were grafted into a human IgG scaffold, and $K_D$ determination was performed by SPR (Pioneer FE) or Octet (Red96e) at 25° C. or 37° C. All values shown in Table 5 are ×10$^{-9}$ M. Antibodies were captured on the chip surface using anti-human Fc antibody (SPR) or AHC sensor (Octet). Human or mouse CTLA-4 was the analyte as indicated in Table 5.

TABLE 5

| KD (nM) for IgG antibodies to human or mouse CTLA-4 | | | | | |
| --- | --- | --- | --- | --- | --- |
| | | 25 deg C. | | 37 deg C. | |
| VH | VL | hCTLA-4 | mCTLA-4 | hCTLA-4 | mCTLA-4 |
| 78-8D2 HC (SEQ ID NO: 60) | 78-8 LC (SEQ ID NO: 63) | 0.41 | 0.32 | 0.67 | 0.40 |
| 78-8D4 HC (SEQ ID NO: 61) | 78-8 LC (SEQ ID NO: 63) | 0.39 | 0.27 | 0.39 | 0.27 |
| 78-8D22 HC (SEQ ID NO: 62) | 78-8 LC (SEQ ID NO: 63) | 0.46 | 0.39 | 0.44 | 0.53 |
| 78-24D1V HC (SEQ ID NO: 64) | 78-24 LC (SEQ ID NO: 67) | 1.6 | 0.18 | 1.5 | 0.23 |
| 78-24D17V HC (SEQ ID NO: 65) | 78-24 LC (SEQ ID NO: 67) | 0.84 | 0.34 | 0.67 | 0.33 |
| 78-24D22V HC (SEQ ID NO: 66) | 78-24 LC (SEQ ID NO: 67) | 1.4 | 0.19 | 1.3 | 0.27 |

13

The inventors further investigated antibody (IgG1) blocking CD80/CTLA4 complex by BLI using Human CTLA-4/human CD80 or mouse CTLA-4/mouse CD80. Here, an Octet Red96e instrument was used to test the ability of αCTLA-4 antibodies to block CD80 binding to CTLA-4. Briefly, biotinylated CTLA-4 was immobilized onto SA biosensors (Molecular Devices/ForteBio). 10 µg/mL (67 nM) αCTLA-4s were then used to load the CTLA-4 coated biosensor. Finally, 250 nM CD80 was used to test binding to CTLA-4 in the presence of αCTLA-4 antibodies, and exemplary results are shown in FIG. 1.

Following the above in vitro studies, the inventors then set out to perform various in vivo experiments to investigate the antitumoral activity of selected IgG constructs. Specifically, the inventors tested in a B16F10 mouse tumor model intratumoral immunization using yeast lysate (pTK170, yeast expressing tumor specific neoepitopes), an anti-OX40 antibody, and selected anti-CTLA-4 antibodies as shown. Four groups of animals were used: 1. PBS; 2. pTK170+aOX40+a-CTLA4-7 (SEQ ID NO:68, SEQ ID NO:69); 3. pTK170+aOX40+a-CTLA4-8 (SEQ ID NO:70, SEQ ID NO:71); and 4. pTK170+aOX40+a-CTLA4-9H10. The administered dose of pTK170 yeast was 5 YU/injection, and anti-OX40 and anti-CTLA4 were administered at 100 ug each per injection.

Figure 2A:
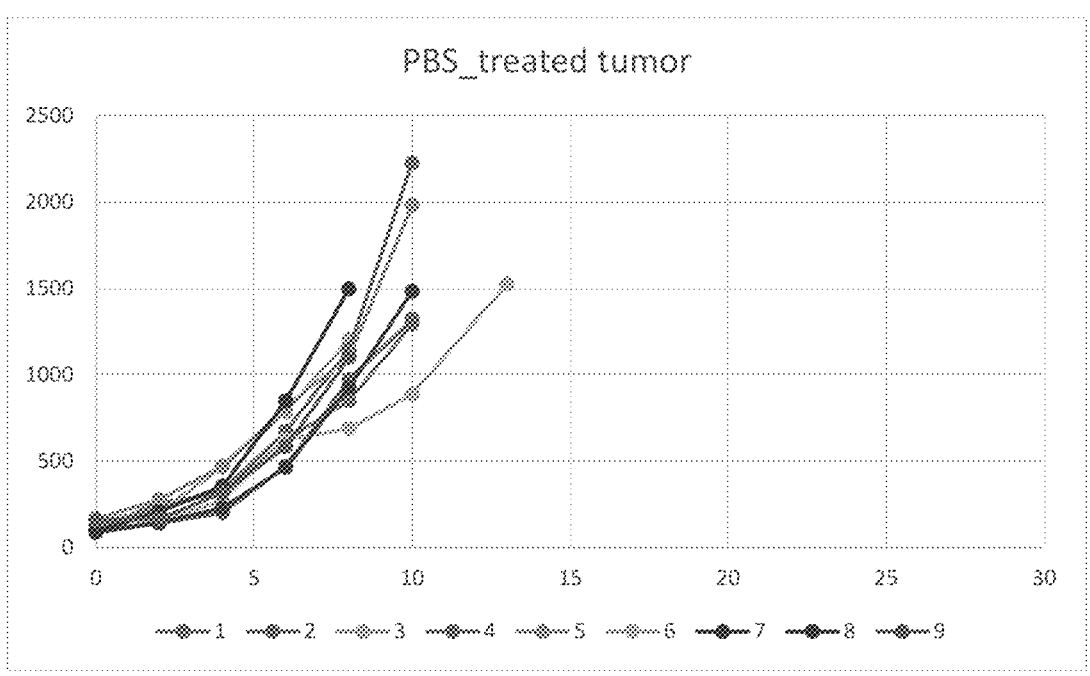
FIGS. 2A-2D depict exemplary results for treated tumors receiving anti-CTLA-4 antibodies and control as presented herein.
Figure 2B:
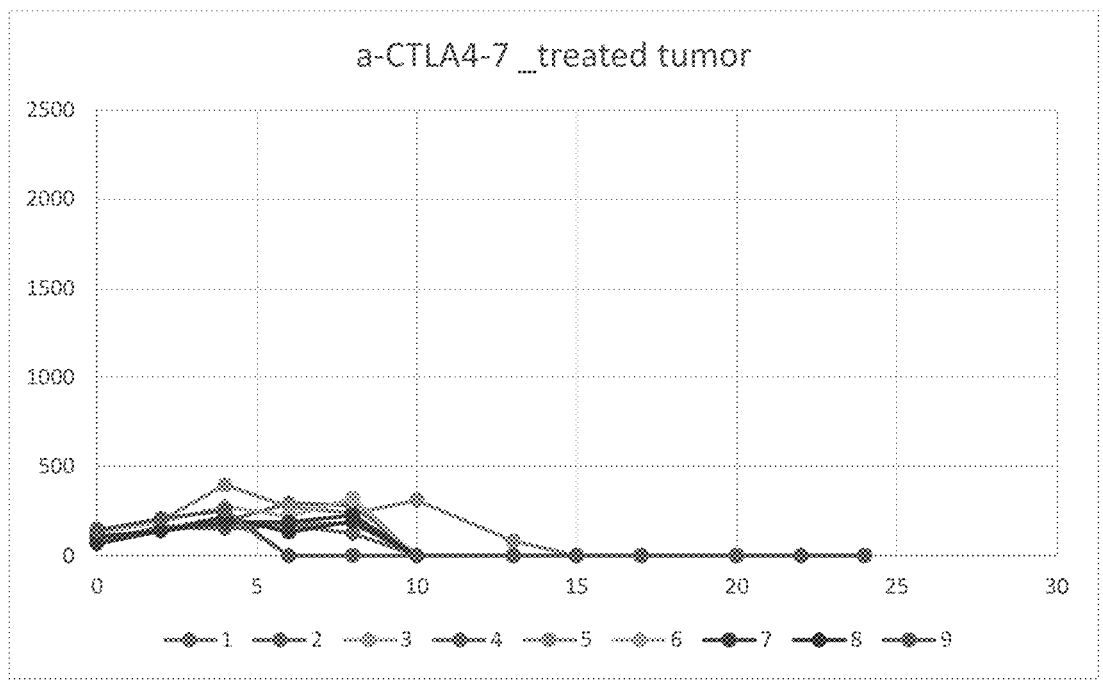
Figure 2C:
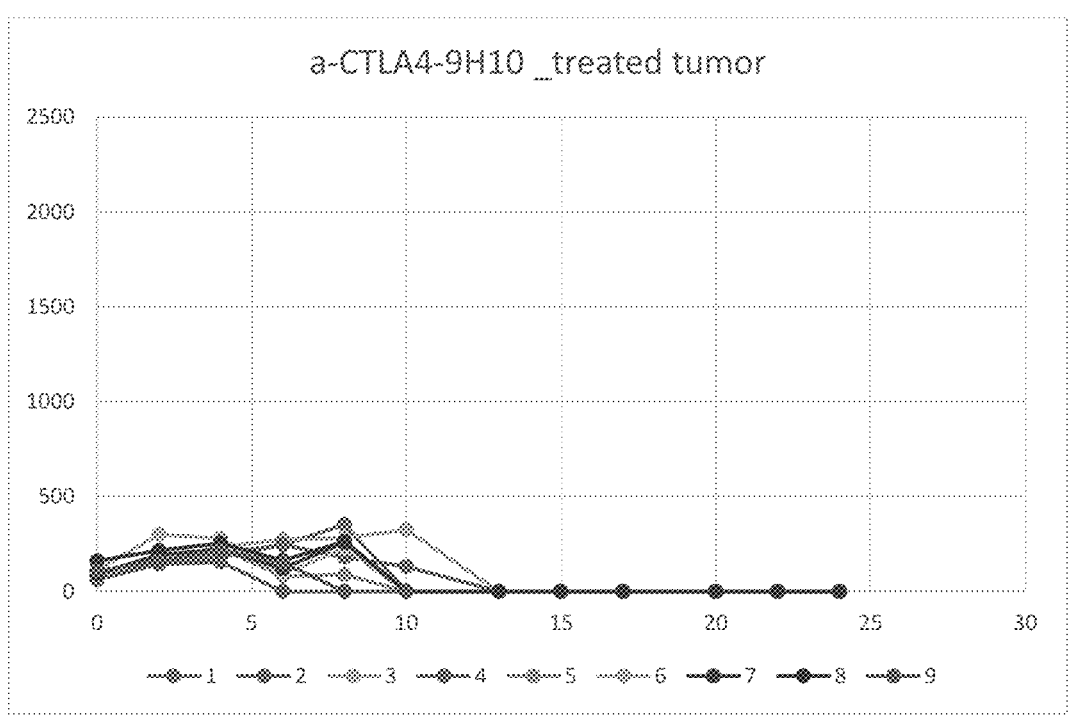
Figure 2D:
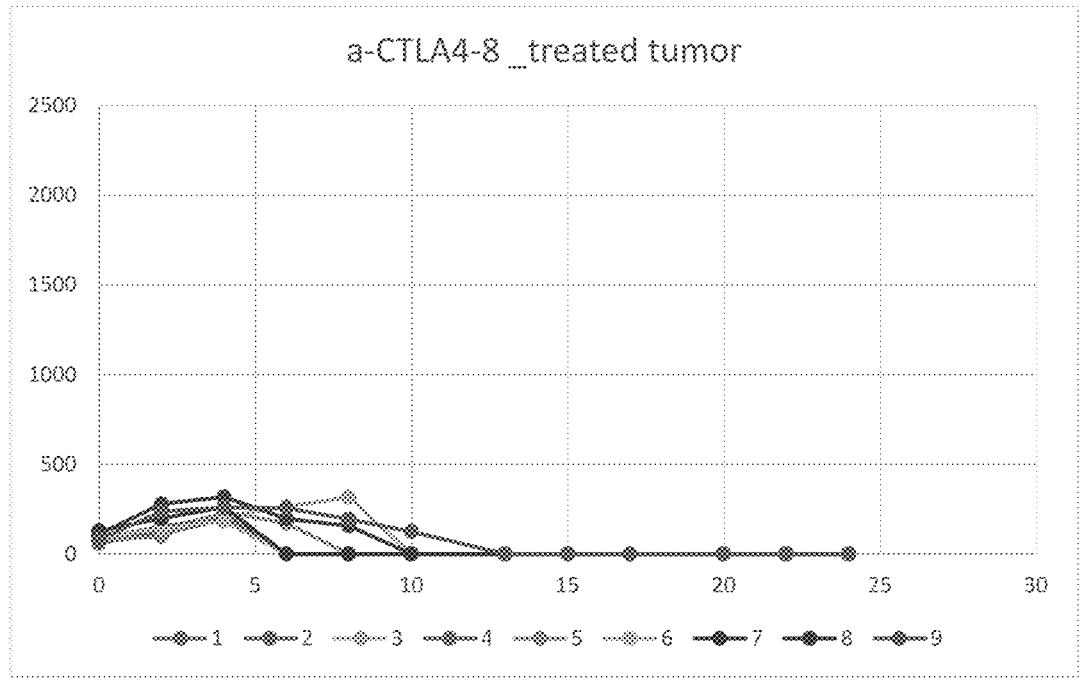
Figure 2E:
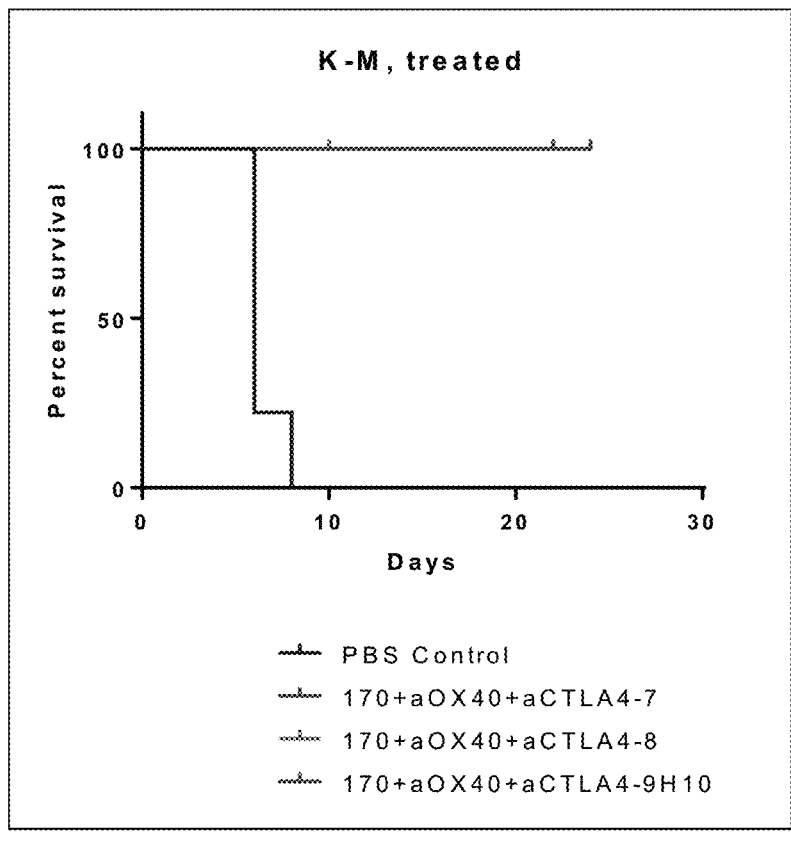
FIG. 2E is a Kaplan Meier plot for the treatment groups of FIGS. 2A-2D.
Figure 3A:
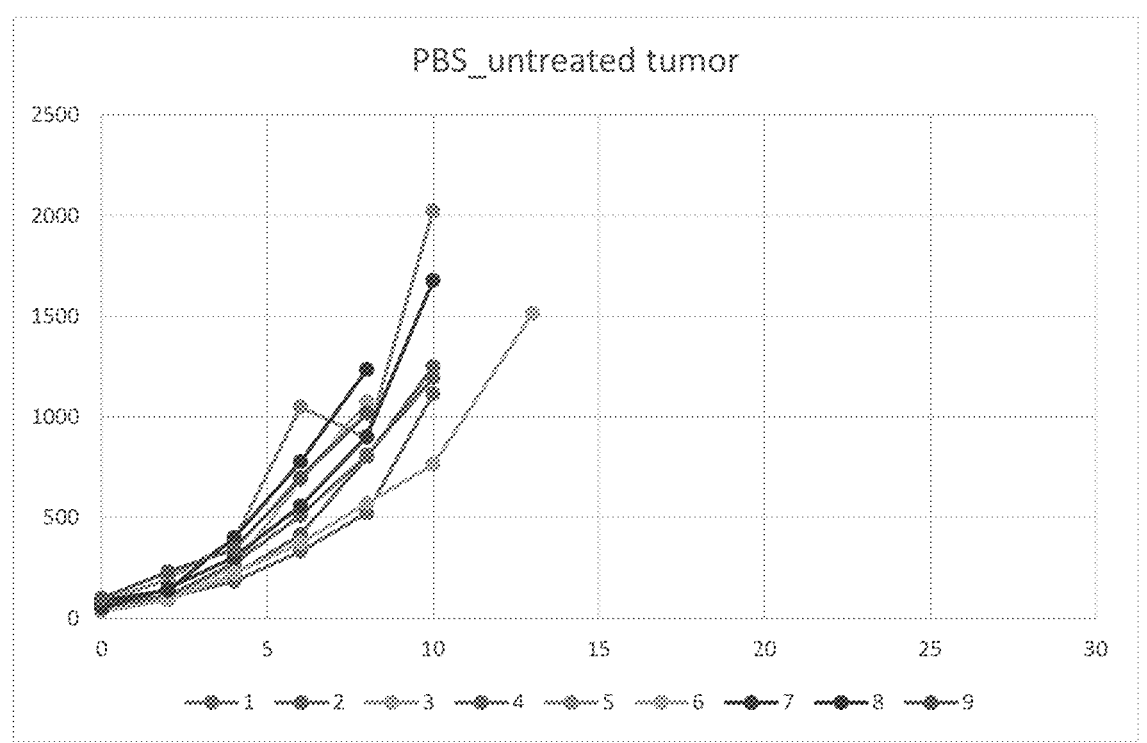
FIGS. 3A-3D depict exemplary results for untreated tumors receiving anti-CTLA-4 antibodies and control as presented herein.
Figure 3B:
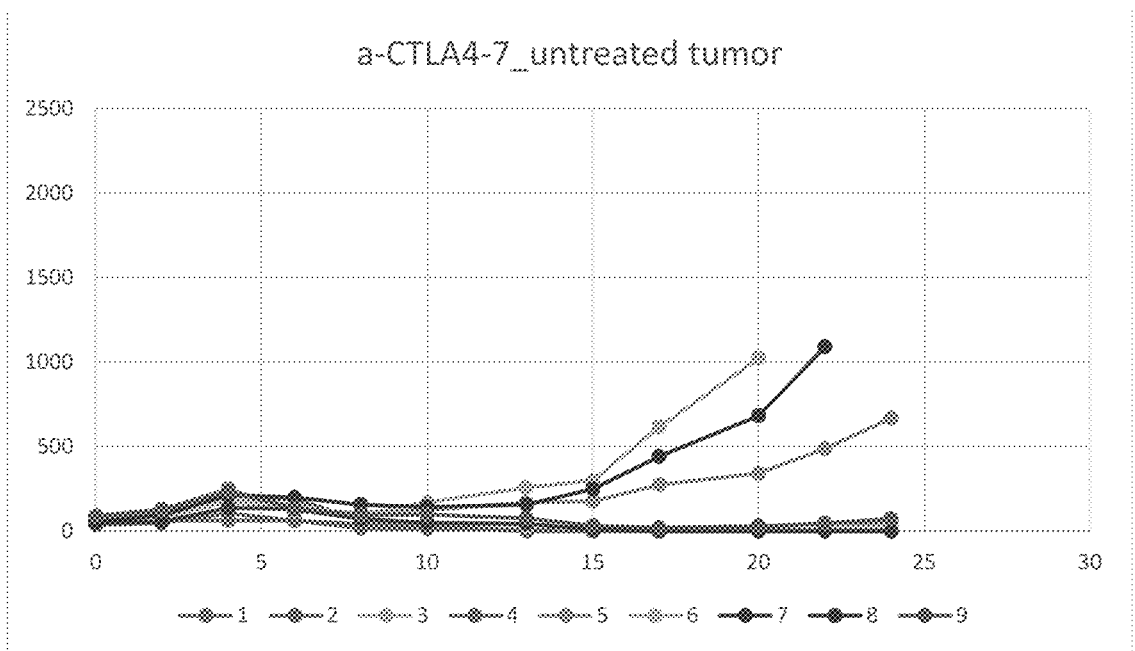
Figure 3C:
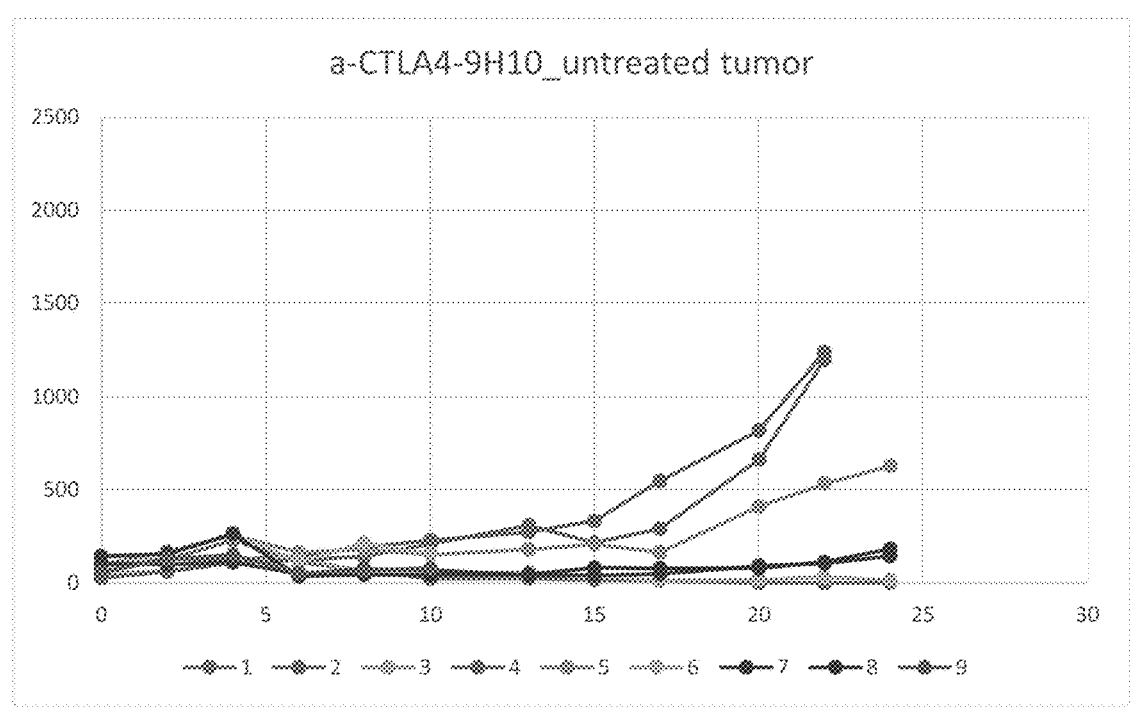
Figure 3D:
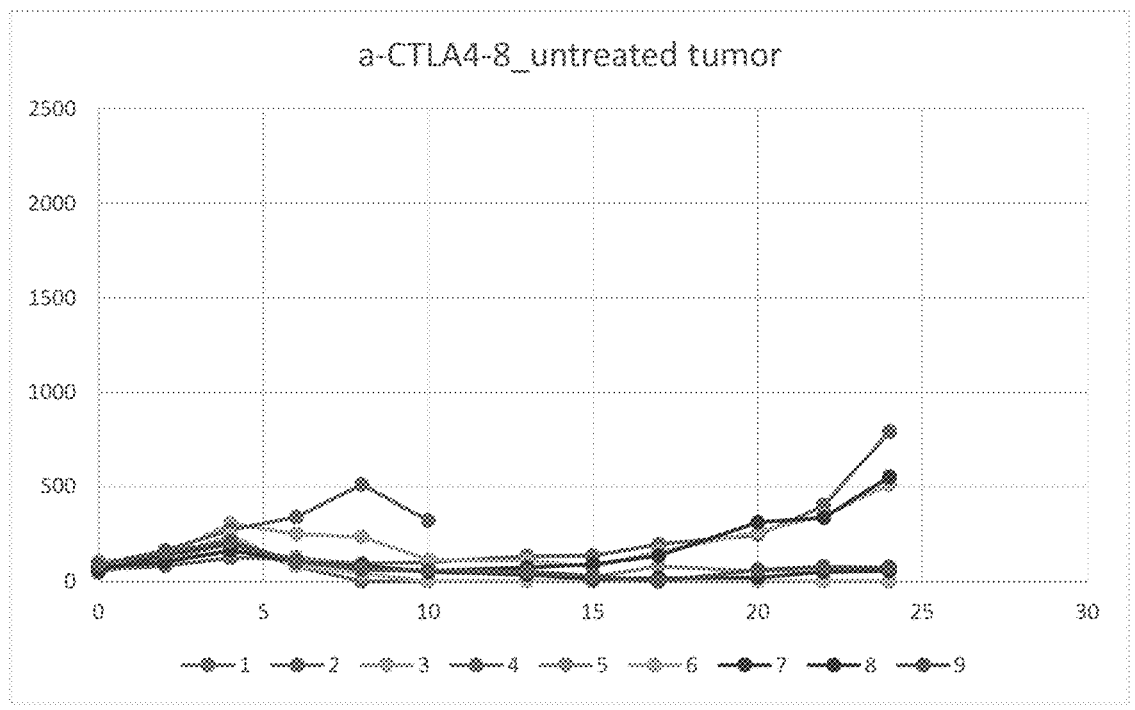
Figure 3E:
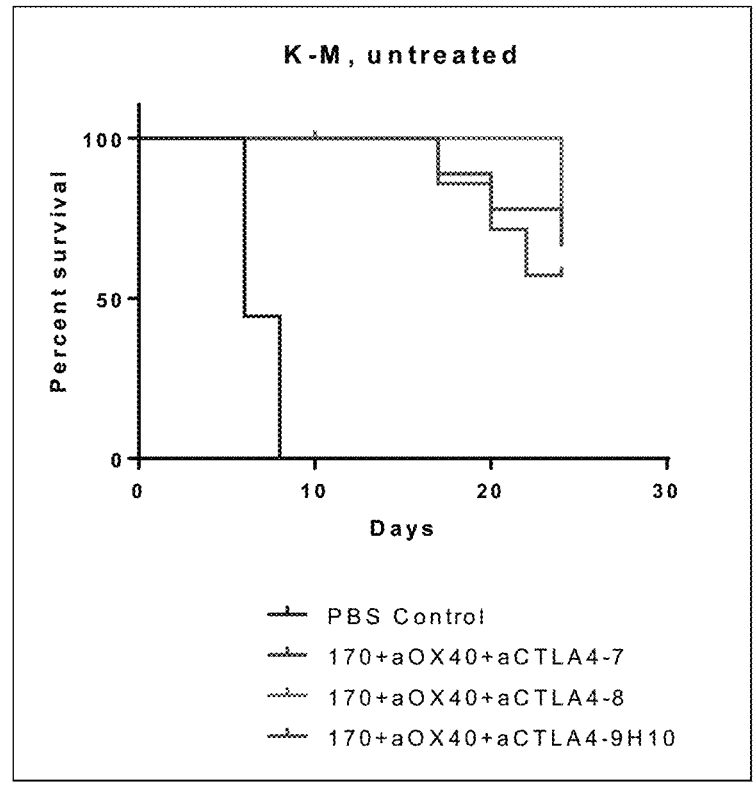
FIG. 3E is a Kaplan Meier plot for the treatment groups of FIGS. 3A-3D.

Exemplary results for tumor volumes are shown in FIGS. 2A-2D, and a Kaplan-Meyer Plot for the animals is provided in FIG. 2E. As can be readily seen, all anti-CTLA4 groups (FIGS. 2B-2D) significantly reduce the tumor growth for both treated and untreated tumors compared to PBS (FIG. 2A). There are no statistically significant differences as yet between clone 7, 8 and 9H10 at the 100 ug dose. Non-injected tumor volumes are shown in FIGS. 3A-3D, with FIG. 3A being the PBS control, and FIGS. 3B-3D showing treatment with anti-CTLA4 compounds. The corresponding Kaplan-Meyer Plot for the animals is provided in FIG. 3E.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An antibody or fusion protein comprised thereof, comprising: a variable heavy chain (VH) segment and a variable light chain (VL) segment respectively consisting of SEQ ID NO:60 and SEQ ID NO: 63, SEQ ID NO:61 and SEQ ID NO:63, SEQ ID NO: 62 and SEQ ID NO:63, SEQ ID NO:64 and SEQ ID NO:67, SEQ ID NO:65 and SEQ ID NO:67, SEQ ID NO:66 and SEQ ID NO:67, SEQ ID NO: 68 and SEQ ID NO:69, or SEQ ID NO:70 and SEQ ID NO:71.

2. The antibody of claim 1 comprising a variable heavy chain (VH) segment and a variable light chain (VL) segment respectively consisting of SEQ ID NO:60 and SEQ ID NO: 63, SEQ ID NO:61 and SEQ ID NO:63, SEQ ID NO:62 and SEQ ID NO:63, SEQ ID NO:64 and SEQ ID NO:67, SEQ ID NO:65 and SEQ ID NO:67, SEQ ID NO:66 and SEQ ID NO:67, SEQ ID NO: 68 and SEQ ID NO:69, or SEQ ID NO:70 and SEQ ID NO:71.

3. An antibody, comprising a heavy chain comprising a first amino acid sequence of SEQ ID NO. 68 and a light chain comprising a second amino acid sequence of SEQ ID NO. 69, or a heavy chain comprising a first amino acid sequence of SEQ ID NO. 70 and a light chain comprising a second amino acid sequence of SEQ ID NO. 71.

4. A recombinant nucleic acid, comprising: a first nucleic acid segment encoding a variable heavy chain (VH) peptide sequence and second nucleic acid segment encoding a variable light chain (VL) peptide sequence, wherein the VH and VL peptide sequences combine to form an antibody, scfv, or fusion proteins derived therefrom, and wherein the VH and VL peptides respectively consist of SEQ ID NO:60 and SEQ ID NO:63, SEQ ID NO:61 and SEQ ID NO:63, SEQ ID NO:62 and SEQ ID NO:63, SEQ ID NO: 64 and SEQ ID NO:67, SEQ ID NO: 65 and SEQ ID NO:67, SEQ ID NO: 66 and SEQ ID NO:67, SEQ ID NO: 68 and SEQ ID NO:69, or SEQ ID NO: 70 and SEQ ID NO:71; and wherein the first and second segments are optionally in a bicistronic arrangement.

5. A recombinant nucleic acid, comprising: a first nucleic acid segment encoding a first amino acid sequence of SEQ ID NO. 68 and second nucleic acid segment encoding a second amino acid sequence of SEQ ID NO. 69, or a first nucleic acid segment encoding a first amino acid sequence of SEQ ID NO. 70 and a second nucleic acid segment encoding a second amino acid sequence of SEQ ID NO. 71.

6. The recombinant nucleic acid of claim 4 further comprising a third segment encoding a polypeptide that encodes at least a portion of a N-803 or TxM, wherein the N-803 or TxM, when expressed in the cell, has an antigen binding domain that comprises an scfv peptide encoded by the first and second nucleic acid segment.

7. A method of reducing immune suppression in a patient having a tumor, comprising: administering to the patient a pharmaceutical composition including an antibody or fusion protein of any one of claims 1-3; and wherein the pharmaceutical composition is administered to the patient in a dose and a schedule effective to reduce immune suppression in a tumor microenvironment.

8. A method of using an antibody or fusion protein of any one of claims 1-3 for treating a cancer and/or reducing immune suppression in a patient having a tumor, comprising: administering to the patient the antibody or fusion protein at a dose and schedule effective to treat the tumor and/or reduce immune suppression in a tumor microenvironment.

* * * * *